US007166461B2

(12) United States Patent
Schwartz et al.

(10) Patent No.: US 7,166,461 B2
(45) Date of Patent: Jan. 23, 2007

(54) POLYNUCLEOTIDES ENCODING A SUPER-ACTIVE PORCINE GROWTH HORMONE RELEASING HORMONE ANALOG

(75) Inventors: Robert J. Schwartz, Houston, TX (US); Ruxandra Draghia-Alki, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 728 days.

(21) Appl. No.: 10/262,141

(22) Filed: Oct. 1, 2002

(65) Prior Publication Data

US 2003/0129172 A1 Jul. 10, 2003

Related U.S. Application Data

(62) Division of application No. 09/624,268, filed on Jul. 24, 2000, now Pat. No. 6,551,996.

(60) Provisional application No. 60/145,624, filed on Jul. 26, 1999.

(51) Int. Cl.
*C12N 15/63* (2006.01)
*C12N 15/18* (2006.01)

(52) U.S. Cl. ................................ 435/320.1; 536/23.51

(58) Field of Classification Search ............ 536/24.51, 536/23.51; 435/320.1
See application file for complete search history.

(56) References Cited

U.S. PATENT DOCUMENTS

| | | | |
|---|---|---|---|
| 4,410,512 | A | 10/1983 | Bowers |
| 4,839,344 | A | 6/1989 | Bowers et al. |
| 5,023,322 | A | 6/1991 | Kovacs et al. |
| 5,036,045 | A | 7/1991 | Thorner |
| RE33,699 | E | 9/1991 | Drengler |
| 5,084,442 | A | 1/1992 | Felix et al. |
| 5,137,872 | A | 8/1992 | Seely et al. |
| 5,298,422 | A | 3/1994 | Schwartz et al. |
| 5,374,544 | A | 12/1994 | Schwartz et al. |
| 5,486,505 | A | 1/1996 | Bowers et al. |
| 5,696,089 | A | 12/1997 | Felix et al. |
| 5,756,264 | A | 5/1998 | Schwartz et al. |
| 5,776,901 | A | 7/1998 | Bowers et al. |
| 5,792,747 | A | 8/1998 | Schally et al. |
| 5,846,936 | A | 12/1998 | Felix et al. |
| 5,847,066 | A | 12/1998 | Coy et al. |
| 5,854,211 | A | 12/1998 | Johansen et al. |
| 6,110,932 | A | 8/2000 | Carpino et al. |
| 6,123,964 | A | 9/2000 | Asgharnejad et al. |
| 6,127,341 | A | 10/2000 | Hansen et al. |

FOREIGN PATENT DOCUMENTS

| | | |
|---|---|---|
| WO | WO 92/00095 A1 | 1/1992 |
| WO | WO 99/05300 A2 | 2/1999 |

OTHER PUBLICATIONS

Campbell, Robert M., et al., "Rational Design, Synthesis, and Biological Evaluation of Novel Growth Hormone Releasing Factor Analogues". Biopolymers (Peptide Science), 1995, vol. 37, pp. 67-88.

Draghia-Akli, Ruxandra. et al., "Myogenic Expression of an Injectable Protease-Resistant Growth Hormone-Releasing Hormone Augments Long-Term Growth in Pigs". Nature Biotechnology, Dec. 1999, vol. 17, pp. 1179-1183.

Pomes A., et al., *Solubilization & characterization of a growth hormone secretagogue receptor from porcine anterior pituitary membranes*, Biochemical & Biophysical Research Communications, Article 1275, 1996, pp. 939-945, vol. 225.

Pong, S-S., et al., *Identification of a new g-protein-linked receptor for growth hormone secretagogues*, Molecular Endocrinology, 1996, pp. 57-61, The Endocrine Society.

Anderson, et al., Human Gene Therapy, Nature, vol. 392, Supplement, Apr. 30, 1998.

Verma, et al., Gene Therapy—Promises, Problems and Prospects, Nature, vol. 389, pp. 239-242, Sep. 18, 1997.

Scanlon MF et al., *Regulation of Growth Hormone Secretion*, Hormone Research 1996, pp. 149-154, vol. 46, S. Karger AG Basel.

Skuse D et al., *Quality of life in Turner syndrome is related to chromosomal constitution: implications for genetic counselling and management*, Acta Paediatr Suppl 1999, pp. 110-113, vol. 428, Scandinavian Univ. Press.

D'Costa AP et al., *The regulation and mechanisms of action of growth hormone and insulin-like growth factor 1 during normal ageing*. J. Reprod. Fert. Suppl. 1993, pp. 87-98, vol. 46, Journals of Reproduction & Fertility Ltd., Great Britain.

Bercu BB et al., *Growth hormone secretagogues in children with altered growth*, Acta Paediatr Suppl 1997, pp. 102-106, vol. 423, Scandinavian Univ. Press.

Gesundheit N et al., *Endocrine Therapy with Recombitant Hormones and Growth Factors*, Molecular Endocrinology: Basic Concepts & Clinical Correlations, 1995, Ch. 30, pp. 491-507, Raven Press, Ltd., New York.

Erling A, *Methodological considerations in the assessment of health-related quality of life in children*, Acta Paediatr Suppl 1999, pp. 106-107, vol. 428, Scandinavian Univ. Press.

(Continued)

*Primary Examiner*—Robert C. Hayes
(74) *Attorney, Agent, or Firm*—Jackson Walker L.L.P.

(57) ABSTRACT

Inadequate growth due to deficiencies in growth hormone (GR), growth hormone releasing hormone (GHRH), or genetic diseases can be ameliorated utilizing recombinant protein therapy with a novel GHRH analog having a sequence (SEQ ID NO:1). Also included is (1) a method of treating growth hormone-related deficiencies associated with the growth hormone pathway; (2) a method for treating growth hormone-related deficiencies associated with genetic disease; (3) a method to improve growth performance in an animal; (4) a method of treating an animal having a growth deficiency disease; (5) a method of increasing the efficiency of an animal used for food; and (6) a method to enhance growth in an animal.

3 Claims, 7 Drawing Sheets

OTHER PUBLICATIONS

Savage MO et al., *Growth in Crohn's disease*, Acta Paediatr Suppl 1999, pp. 89-92, vol. 428, Scandinavian Univ. Press.

Parks JS et al., *Growth Hormone Deficiency*, Molecular Endocrinology Basic Concepts & Clinical Correlations 1995, Ch. 29, pp. 473-490, Raven Press, Ltd., New York.

Thorner MO et al., *Extrahypothalamic Browth-Hormone-Releasing Factor (GRF) Secretion Is a Rare Cause of Acromegaly: Plasma GRF Levels in 177 Acromegalic Patients*, Journal of Clinical Endocrinology & Metabolism 1984, pp. 846-849, vol. 59, No. 5, The Endocrine Society, USA.

Corpas E et al., *Continuous Subcutaneous Infusions of Growth Hormone (GH) Releasing Hormone 1-44 for 14 Days Increase GH and Insulin-Like Growth Factor-1 Levels in Old Men*; Journal of Clinical Endocrinology & Metabolism, 1993, pp. 134-138, vol. 76, No. 1, The Endocrine Society, USA.

Esch FS et al., *Characterization of a 40 residue peptide from a human pancreatic tumor with growth hormone releasing activity*, Biochemical & Biophysical Research Communications, Nov. 16, 1982, pp. 152-158, vol. 109, No. 1, Academic Press.

Frohman LA et al., *Metabolic Clearance & Plasma Disappearance Rates of Human Pancreatic Tumor Growth Hormone Releasing Factor in Man*, J. Clin. Invest., May 1984, pp. 1304-1311, vol. 73, The American Society for Clinical Investigation, Inc.

Corpas E et al., *Human growth hormone & human aging*, Endocrine Reviews, 1993, pp. 20-39, vol. 14, No. 1, The Endocrine Society, USA.

Campbell RM et al., *GRF analogs & fragments: correlation between receptor binding, activity & structure*, Peptides, 1991, pp. 569-574, vol. 12, Pergamon Press plc, USA.

Martin RA et al., *Dipeptidyl peptidase IV (DPP-IV) from pig kidney cleaves analogs of bovine growth hormone-releasing factor (bGRF) modified at position 2 with Ser, Thr or Val. extended DPP-IV substrate specificity?*, Biochimica et Bioshysica Acta, 1993, pp. 252-260, vol. 1164, Elsevier Science Publishers BV.

Su C-M et al., *In vitro stability of growth hormone releasing factor (GRF) analogs in porcine plasma*, Horm.metab.Res, 1991, pp. 15-21, vol. 23, Georg Thieme Verlag Stuttgart NY.

Kubiak TM et al., *In vitro metabolic degradation of a bovine growth hormone-releasing factor analog LEU27-bGRF(1-29)$NH_2$ in bovine & porcine plasma*, Drug Metabolism & Disposition 1989, pp. 393-397, vol. 17, No. 4, The American Society for Pharmacology & Experimental Therapeutics, USA.

Frohman MA et al., *Cloning & characterization of mouse growth hormone-releasing hormone (GRH) complementary DNA: increased GRH messenger RNA levels in the growth hormone-deficient lit/lit mouse*, Molecular Endocrinology, 1989, pp. 1529-1536, 0888-8809/89, The Endocrine Society.

Aihara H et al., *Gene transfer into muscle by electroporation in vivo*, Nature Biotechnology, Sept. 1998, pp. 867-869, vol. 16.

Li X et al., *Synthetic muscle promoters: activities exceeding naturally occurring regulatory sequences*, Nature Biotechnology, Mar. 1999, pp. 241-245, vol. 17.

Draghia-Akli R et al., *Enhanced growth by ectopic expression of growth hormone releasing hormone using an injectable myogenic vector*, Nature Biotechnology, Nov. 1997, pp. 1285-1289, vol. 15.

Tanner JW et al., *Modulation of growth hormone (GH) secretion and GH mRNA levels by GH-releasing factor, somatostatin and secretagogues in cultured bovine adenohypophysial cells*, Journal of Endocrinology, 1990, pp. 109-115, vol. 125, Journal of Endocrinology Ltd., Great Britain.

Coleman ME, *Myogenic vector expression of insulin-like growth factor 1 stimulates muscle cell differentiation and myofiber hypertrophy in transgenic mice*, The Journal of Biological Chemistry, May 19, 1995, pp. 12109-12116, vol. 270, No. 20, The American Society for Biochemistry & Molecular Biology, Inc.

*FIG. 1A*
YADAIFTNSYRKVLGQLSARKLLQDIMSRQQGERNQEQGA-OH porcine wild-type
HVDAIFTNSYRKVLAQLSARKLLQDILNRQQGERNQEQGA-OH HV-GHRH
*FIG. 1B*
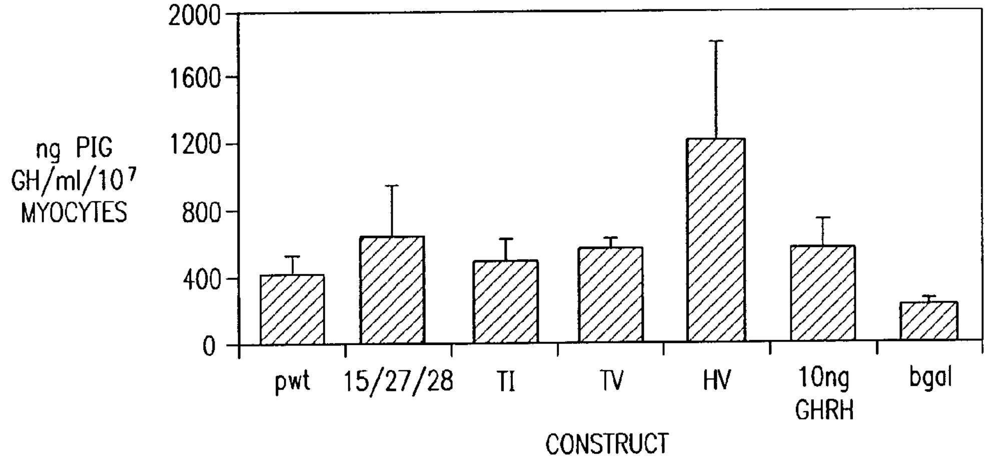
*FIG. 1C*
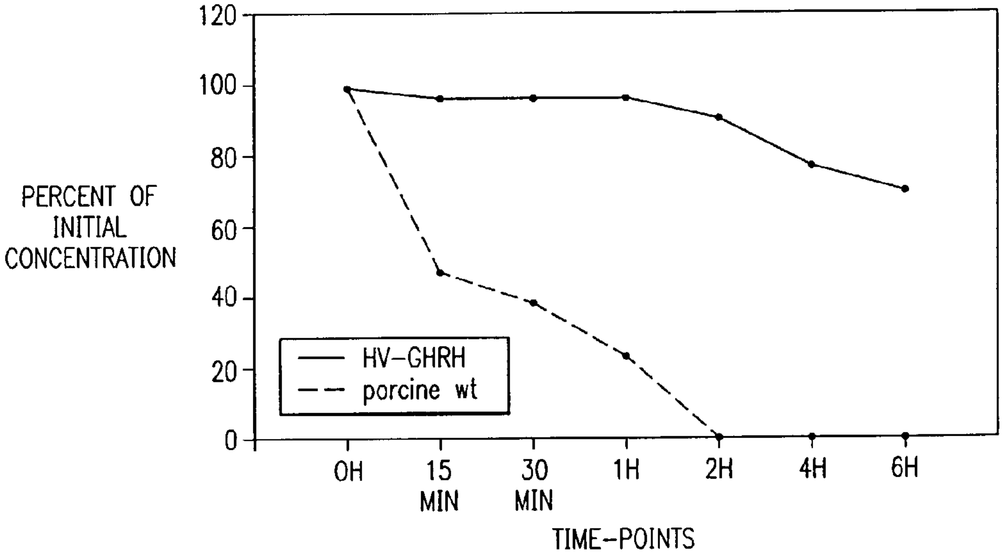

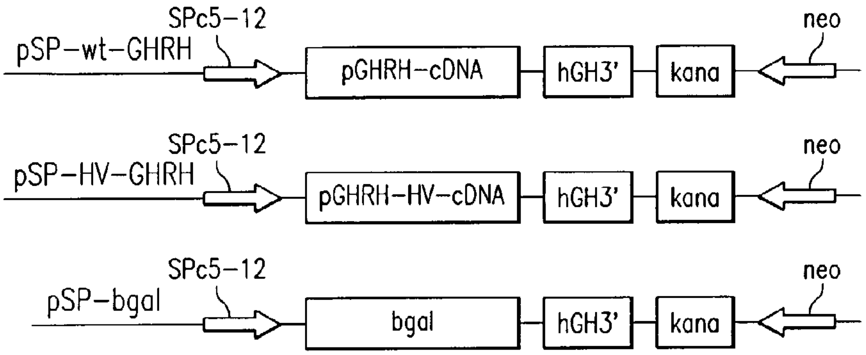
FIG. 2A
FIG. 2B
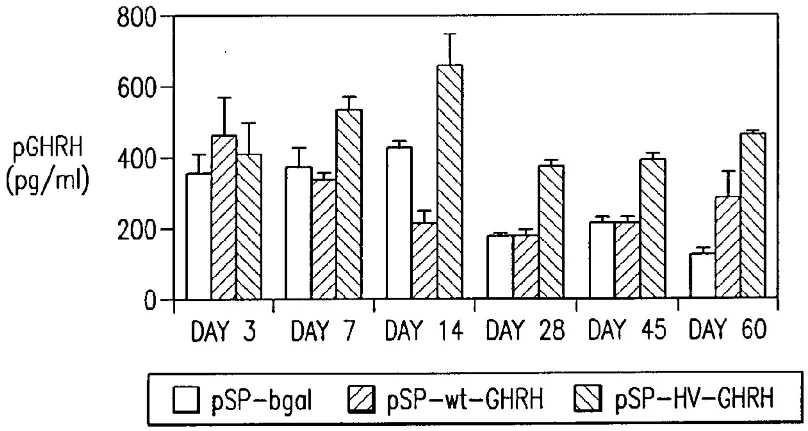
FIG. 2C
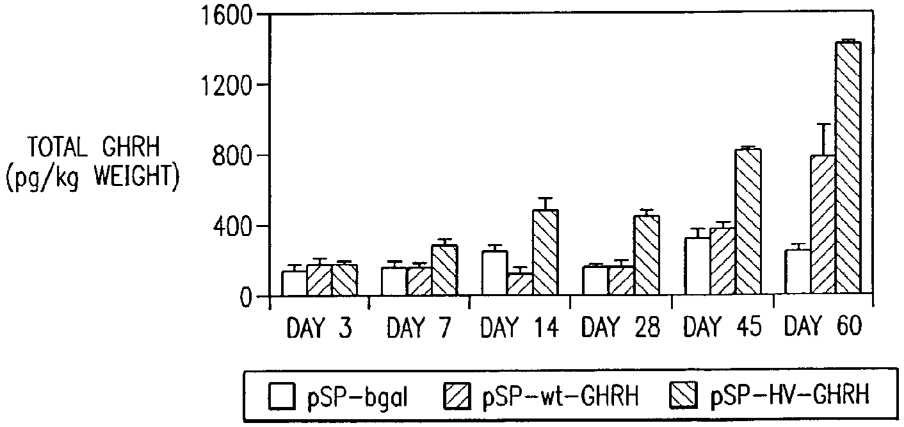

POLYNUCLEOTIDES ENCODING A SUPER-ACTIVE PORCINE GROWTH HORMONE RELEASING HORMONE ANALOG

This application claims priority to U.S. application Ser. No. 09/624,268 filed Jul. 24, 2000, now U.S. Pat. No. 6,551,996, which claims the benefit of U.S. Provisional Application Ser. No. 60/145,624, filed Jul. 26, 1999.

FIELD OF THE INVENTION

This invention relates to the treatment of growth deficiencies; the improvement of growth performance; the stimulation of production of growth hormone in an animal at a level greater than that associated with normal growth; and the enhancement of growth utilizing the administration of a growth hormone releasing hormone analog. Furthermore it relates to the application of a nucleotide sequence encoding said growth hormone releasing hormone analog regulated by a muscle-specific promoter into muscle tissue, particularly using gene therapy techniques.

BACKGROUND OF THE INVENTION

The growth hormone (GH) pathway is composed of a series of interdependent genes whose products are required for normal growth. The GH pathway genes include: (1) ligands, such as GH and insulin-like growth factor-I (IGF-I); (2) transcription factors such as prophet of pit 1, or prop 1 and pit 1; (3) agonists and antagonists, such as growth hormone releasing hormone (GHRH) and somatostatin, respectively; and (4) receptors, such as GHRH receptor (GHRH-R) and the GH receptor (GH-R). These genes are expressed in different organs and tissues, including the hypothalamus, pituitary, liver, and bone. Effective and regulated expression of the GH pathway is essential for optimal linear growth, as well as homeostasis of carbohydrate, protein, and fat metabolism. GH synthesis and secretion from the anterior pituitary is stimulated by GHRH and inhibited by somatostatin, both hypothalamic hormones. The central role of GH in controlling somatic growth in humans and other vertebrates, and the physiologically relevant pathways regulating GH secretion from the pituitary are well known. GH increases production of IGF-I, primarily in the liver, and other target organs. IGF-I and GH, in turn, feedback on the hypothalamus and pituitary to inhibit GHRH and GH release. GH has both direct and indirect actions on peripheral tissues, the indirect effects being mediated mainly by IGF-I.

There is a wide spectrum of clinical conditions, both in children and adults, in which linear growth (prepubertal patients) or body composition are compromised, and which respond to GH or GHRH therapy. In all instances the GHRH-GH-IGF-I axis is functional, but not necessarily operating at optimal sensitivity or responsiveness for a variety of possible reasons.

The principal feature of GH deficiencies in children is short stature. Similar phenotypes are produced by genetic defects at different points in the GH axis (Parks et al., 1995), as well as non-GH-deficient short stature. Non-GH-deficiencies have different etiology: (1) genetic diseases, Turner syndrome (Jacobs et al., 1990; Skuse et al., 1999), hypochondroplasia (Tanaka et al., 1998; Key and Gross, 1996), and Crohn's disease (Savage et al., 1999); and (2) intrauterine growth retardation (Albanese and Stanhope, 1997; Azcona et al., 1998); and (3) chronic renal insufficiency (Sohmiya et al., 1998; Benfield and Kohaut, 1997). Cases where the GH axis is unaffected (i.e. patients have normal hormones, genes and receptors) account for more than 50% of the total cases of growth retardation. In these cases GHRH or GH therapy has been shown to be effective (Gesundheit and Alexander, 1995).

Reduced GH secretion from the anterior pituitary causes skeletal muscle mass to be lost during aging from 25 years to senescence. The GHRH-GH-IGF-1 axis undergoes dramatic changes through aging and in the elderly (D'Costa et al., 1993) with decreased GH production rate and GH half-life, decreased IGF-1 response to GH and GHRH stimuli leading to loss of skeletal muscle mass (sarcopenia), osteoporosis, and increase in fat and decrease in lean body mass (Bartke, 1998). Previous studies have shown that in a significant number of normal elderly persons, GH and IGFs levels in serum are significantly reduced by 70–80% of their teenage level (Corpas et al., 1993; Iranmanesh et al., 1991). It has been demonstrated that the development of sarcopenia can be offset by GH therapy. However, this remains a controversial therapy in the elderly because of its cost and frequent side effects.

The production of recombinant proteins allows a useful tool for the treatment of these conditions. Although GH replacement therapy is widely used in patients with growth deficiencies and provides satisfactory growth, and may have positive psychological effects on the children being treated (Rosenbaum and Saigal, 1996; Erling, 1999), this therapy has several disadvantages, including an impractical requirement for frequent administration of GH (Monti et al., 1997; Heptulla et al., 1997) and undesirable secondary effects (Blethen et al., 1996; Watkins, 1996; Shalet et al., 1997; Allen et al, 1997).

It is well established that extracranially secreted GHRH, as mature peptide or truncated molecules (as seen with pancreatic islet cell tumors and variously located carcinoids) are often biologically active and can even produce acromegaly (Esch et al., 1982; Thorner et al., 1984). Administration of recombinant GHRH to GH-deficient children or adult humans augments IGF-1 levels, increases GH secretion proportionally to the GHRH dose, yet still invokes a response to bolus doses of GHRH (Bercu and Walker, 1997). Thus, GHRH administration represents a more physiological alternative of increasing subnormal GH and IGF-1 levels (Corpas et al., 1993).

Although GHRH protein therapy entrains and stimulates normal cyclical GH secretion with virtually no side effects, the short half-life of GHRH in vivo requires frequent (one to three times a day) intravenous, subcutaneous or intranasal (requiring 300-fold higher dose) administration. Thus, as a chronic treatment, GHRH administration is not practical. However, extracranially secreted GHRH, as a processed protein species (Tyr1-40 or Tyr1-Leu44) or even as shorter truncated molecules, are biologically active (Thorner et al., 1984). Importantly, a low level of GHRH (100 pg/ml) in the blood supply stimulates GH secretion (Corpas et al., 1993) and makes GHRH an excellent candidate for gene therapeutic expression. Direct plasmid DNA gene transfer is currently the basis of many emerging gene therapy strategies and thus does not require viral genes or lipid particles (Muramatsu et al., 1998; Aihara and Miyazaki, 1998). Skeletal muscle is a preferred target tissue, because muscle fiber has a long life span and can be transduced by circular DNA plasmids that express over months or years in an immunocompetent host (Davis et al., 1993; Tripathy et al., 1996). Previous reports demonstrated that human GHRH cDNA could be delivered to muscle by an injectable myogenic expression vector in mice where it transiently stimulated GH secretion to a modest extent over a period of two weeks (Draghia-Akli et al., 1997).

Wild type GHRH has a relatively short half-life in the circulatory system, both in humans (Frohman et al., 1984) and in farm animals. After 60 minutes of incubation in plasma 95% of the GHRH(1–44)$NH_2$ is degraded, while incubation of the shorter (1–40)OH form of the hormone, under similar conditions, shows only a 77% degradation of the peptide after 60 minutes of incubation (Frohman et al., 1989). Incorporating cDNA coding for the shorter GHRH, species (1–40)OH, in a gene therapy vector might result in a molecule with a longer half-life in serum, increased potency, and will provide greater GH release in plasmid injected animals. In addition, mutagenesis via amino acid replacement of protease sensitive amino acids could prolong the serum half-life of the hGHRH molecule. Furthermore, the enhancement of biological activity of GHRH is achieved by using super-active analogs which may increase its binding affinity to specific receptors.

There are issued patents which address administering novel GHRH analog proteins (U.S. Pat. Nos. 5,847,066; 5,846,936; 5,792,747; 5,776,901; 5,696,089; 5,486,505; 5,137,872; 5,084,442; 5,036,045; 5,023,322; 4,839,344; 4,410,512; RE33,699) or synthetic or naturally occurring peptide fragments of GHRH (U.S. Pat. Nos. 4,833,166; 4,228,158; 4,228,156; 4,226,857; 4,224,316; 4,223,021; 4,223,020; 4,223,019) for the purpose of increasing release of growth hormone. A GHRH analog containing the following mutations has been reported (U.S. Pat. No. 5,846,936): Tyr at position 1 to His; Ala at position 2 to Val, Leu, or others; Asn at position 8 to Gln, Ser, or Thr; Gly at position 15 to Ala or Leu; Met at position 27 to Nle or Leu; and Ser at position 28 to Asn. The analog of the present invention does not contain all of the amino acid substitutions reported in U.S. Pat. No. 5,846,936 to be necessary for activity.

Although specific embodiments of U.S. Pat. No. 5,756,264 concern gene therapy wherein the therapeutic gene is delivered into myogenic tissue, and one example mentioned in the specification is growth hormone releasing hormone, two important differences differentiate this system from the present invention. First, this invention concerns an analog of growth hormone releasing hormone which differs from the wild type form with significant modifications which improve its function as a GH secretagogue: decreased susceptibility to proteases and increased stability, which would prolong the ability to effect a therapy, and increased biological activity, which would enhance the ability to effect a therapy. In addition, in one aspect of the present invention it utilizes a unique synthetic promoter, termed SPc5-12 (Li et al., 1999), which contains a proximal serum response element (SRE) from skeletal α-actin, multiple MEF-2 sites, MEF-1 sites, and TEF-1 binding sites, and greatly exceeds the transcriptional potencies of natural myogenic promoters. The uniqueness of such a synthetic promoter is a significant improvement over, for instance, issued patents concerning a myogenic promoter and its use (e.g. U.S. Pat. No. 5,374,544) or systems for myogenic expression of a nucleic acid sequence (e.g. U.S. Pat. No. 5,298,422).

Thus, the present invention teaches application of an analog containing mutations which improve the ability to elicit the release of growth hormone. As illustrated in the Examples, said analog succeeds in increasing release of growth hormone despite the absence of the substitution at position 8 to Gln, Ser, or Thr in the analog of the prior art. Furthermore, it provides gene therapy techniques to introduce said analog, whose expression is regulated by a synthetic myogenic promoter, into the preferred choice of skeletal muscle tissue since muscle fiber has a long life span and can be transduced by circular DNA plasmids. This is an improvement over the present art, in which the requirement for frequent administration of GHRH protein precludes it for use as a chronic treatment.

SUMMARY OF THE INVENTION

An embodiment of the present invention is the growth hormone releasing hormone having the amino acid sequence of SEQ ID NO:1.

Additional embodiments of the present invention include: (1) a method for treating growth hormone-related deficiencies associated with the growth hormone pathway; (2) a method for treating growth hormone-related deficiencies associated with genetic disease; (3) a method to improve growth performance in an animal; (4) a method of treating an animal having a growth deficiency disease; (5) a method of increasing the efficiency of an animal used for food; and (6) a method of treating in an animal wasting symptoms associated with burn, trauma, AIDS, or other consumption diseases; (7) a method for stimulating production of growth hormone in an animal at a level greater than that associated with normal growth; and (8) a method of enhancing growth in an animal. All of these methods include the step of introducing a plasmid vector into an animal, wherein said vector comprises a promoter; a nucleotide sequence encoding SEQ ID NO:1; and a 3' untranslated region operatively linked sequentially at appropriate distances for functional expression.

In a preferred embodiment the promoter is a synthetic myogenic promoter and hGH 3' untranslated region is in the 3' untranslated region.

In specific embodiments said vector is selected from the group consisting of a plasmid, a viral vector, a liposome, or a cationic lipid. In further specific embodiments said vector is introduced into myogenic cells or muscle tissue. In a further specific embodiment said animal is a human, a pet animal, a work animal, or a food animal.

An additional embodiment is a pharmaceutical composition for stimulating the release of growth hormone in animals comprising SEQ ID NO:1 in a pharmaceutically acceptable carrier.

Another embodiment of the present invention is the nucleotide sequence encoding the growth hormone-releasing hormone having the amino acid sequence of SEQ ID NO:1.

In an additional embodiment of the present invention there is a method of increasing growth hormone in an animal comprising the step of introducing a therapeutically effective amount of a vector into an animal, said vector comprised of a promoter; a nucleotide sequence encoding SEQ ID NO:1; and a 3' untranslated region operatively linked for functional expression. In a specific embodiment the promoter is a synthetic myogenic promoter. In another specific embodiment the 3' untranslated region is the hGH 3' untranslated region. In another specific embodiment the animal is selected from the group consisting of a human, a pet animal, a food animal and a work animal. In an additional specific embodiment the vector is introduced into myogenic cells. In a further specific embodiment the vector is introduced into muscle tissue of said animal. In another specific embodiment the introduction treats a growth hormone-related deficiency disease associated with the growth hormone pathway. In an additional specific embodiment the deficiency disease is the result of a change in the genetic material in said animal. In a further embodiment the introduction results in improving growth performance in said animal. In another embodiment the introduction increases the efficiency of the animal, wherein the animal is used for food. In an additional embodiment the introduction treats in an animal wasting symptoms associated with burn, trauma, AIDS, or other consumption diseases. In another specific embodiment the introduction results in enhancement of growth of said animal. In another specific embodiment the vector is introduced into said animal in a single administration. In a further specific embodiment the vector is selected from the group consisting of a plasmid, a viral vector, a liposome, and a cationic lipid.

In an additional embodiment of the present invention there is a method of treating growth hormone-related deficiencies associated with the growth hormone pathway in an animal comprising the step of introducing a therapeutically effective amount of a vector into an animal, said vector comprised of a synthetic myogenic promoter; a nucleotide sequence encoding SEQ ID NO:1; and the 3' untranslated region of hGH operatively linked for functional expression.

In another embodiment of the present invention there is a method for stimulating production of growth hormone in an animal at a level greater than that associated with normal growth, said method comprising introducing into said animal an effective amount of a vector, said vector comprising a synthetic myogenic promoter; a nucleotide sequence encoding SEQ ID NO:1; and a 3' untranslated region of hGH operatively linked for functional expression.

Other and further objects, features and advantages would be apparent and eventually more readily understood by reading the following specification and by reference to the company drawing forming a part thereof, or any examples of the presently preferred embodiments of the invention are given for the purpose of the disclosure.

DESCRIPTION OF THE DRAWINGS

FIG. 1A through FIG. 1C demonstrate that GHRH super-active analogs increase GH secretagogue activity and stability. FIG. 1A is a comparison of the porcine wild type (1–40)OH amino acid sequence with the analog HV-GHRH. FIG. 1B shows the effect of the different GHRH species on pig GH release in porcine primary pituitary culture. FIG. 1C demonstrates changes in stability which occur with HV-GHRH and wild type porcine GHRH during a 4 to 6 hour incubation.

FIG. 2A through FIG. 2E demonstrate an increase in GHRH, GH and IGF-I serum levels over two months following single injections of super-active analog GHRH myogenic expression vector. FIG. 2A depicts the constructs which contain the SPc5-12 synthetic promoter and the 3' UTR of GH. As a model of mutated protein, HV-GHRH construct was used and compared with the porcine wild type as a positive control, and with β-galactosidase construct as a negative control. FIG. 2B illustrates relative levels of serum GHRH in pSP-GHRH injected pigs versus placebo injected control pigs. FIG. 2C demonstrates absolute levels of serum GHRH in pSP-GHRH injected pigs versus controls pigs corrected for weight/blood volume increase. FIG. 2D shows variation of GH levels in pSP-HV-GHRH injected pigs. FIG. 2E shows plasma IGF-1 levels following direct intramuscular injection of pSP-GHRH constructs.

FIG. 3A shows the change in average weight in injected pigs over 2 months with pSP-GHRH or pSP-GHRH-HV. FIG. 3B shows the status of feed efficiency in the pSP-GHRH injected pigs versus controls. FIG. 3C is a comparison of a pSP-HV-GHRH injected pig and a placebo injected control pig, 45 days post-injection.

DETAILED DESCRIPTION OF THE INVENTION

Figure 2D:
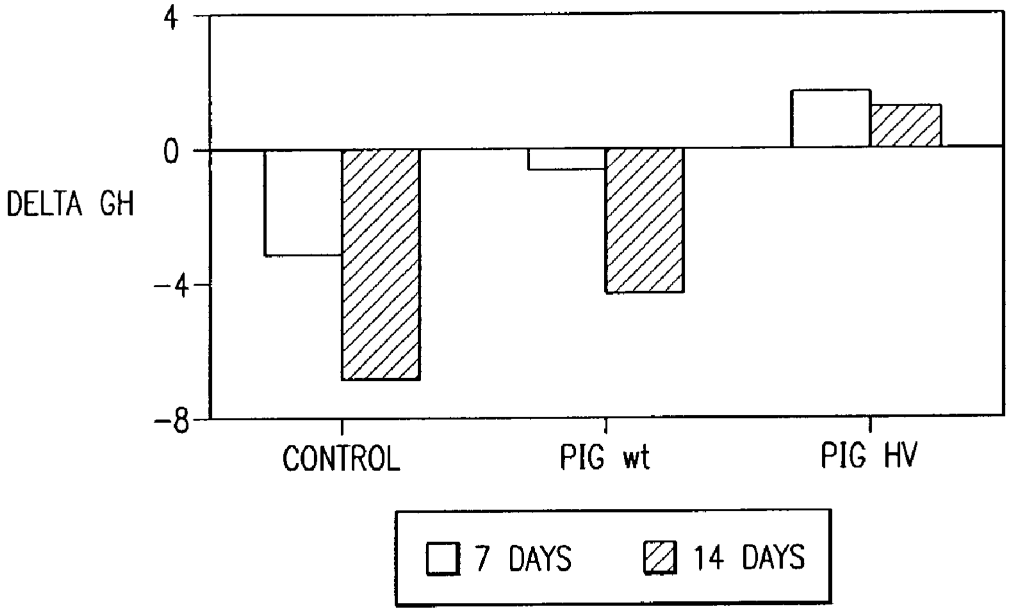

It will be readily apparent to one skilled in the art that various substitutions and modifications may be made in the invention disclosed herein without departing from the scope and spirit of the invention.

The term "animal" as used herein refers to any species of the animal kingdom. In preferred embodiments it refers more specifically to humans, animals used as pets (dogs, cats, horses), animals used for work (horses, cows) and food animals which include animals which produce food (chickens, cows, fish) or are themselves food (frogs, chickens, fish, crabs, lobsters, shrimp, mussels, scallops, goats, boars, cows, lambs, pigs, ostrich, emu, eel) and others well known in the art.

The term "consumption diseases" as used herein are defined as diseases in which one loses weight (mostly muscle mass), loses muscle strength, may have demineralization of bones (involuntary, with no known mechanism), may have a combination of viral/bacterial infection, or may have deregulation of some basic metabolisms. Some examples of such diseases are AIDS, tuberculosis, or cancer.

The term "effective amount" as used herein is defined as the amount of the composition required to produce an effect in a host which can be monitored using several end-points known to those skilled in the art.

The term "efficiency" as used herein is defined as the amount of food an animal eats per day versus the amount of weight gained by said animal.

The term "growth deficiencies" as used herein is defined as any health status, medical condition or disease in which growth is less than normal. The deficiency could be the result of an aberration directly affecting a growth hormone pathway (such as the GHRH-GH-IGF-I axis), indirectly affecting a growth hormone pathway, or not affecting a growth hormone pathway at all.

The term "growth hormone" as used herein is defined as a hormone which relates to growth and acts as a chemical messenger to exert its action on a target cell.

The term "growth hormone releasing hormone" as used herein is defined as a hormone which facilitates or stimulates release of growth hormone.

The term "growth hormone releasing hormone analog" as used herein is defined as a protein which contains amino acid mutations in the naturally occurring form of the amino acid sequence (with no synthetic dextro or cyclic amino acids), but not naturally occurring in the GHRH molecule, yet still retains its function to enhance synthesis and secretion of growth hormone.

The term "myogenic" as used herein refers specifically to muscle tissue.

The term "pharmaceutically acceptable" as used herein refers to a compound wherein administration of said compound can be tolerated by a recipient mammal.

The term "secretagogue" as used herein refers to a natural or synthetic molecule that enhances synthesis and secretion of a downstream—regulated molecule (e.g. GHRH is a secretagogue for GH).

The term "therapeutically effective amount" as used herein refers to the amount of a compound administered wherein said amount is physiologically significant. An agent is physiologically significant if its presence results in technical change in the physiology of a recipient animal. For example, in the treatment of growth deficiencies, a composition which increases growth would be therapeutically effective; in consumption diseases a composition which would decrease the rate of loss or increase the growth would be therapeutically effective. A skilled artisan is aware that a sufficient vector amount is utilized to provide expression of a nucleotide sequence encoding SEQ ID NO:1 to therapeutically effective levels.

The term "treats" as used herein is defined as the act of affecting favorably at least one symptom of a growth deficiency disease or affecting favorably the growth of an animal. A skilled artisan is aware that the term "treats" does not necessarily indicate cure, although a cure of the symptom or symptoms is within the scope of the term treat.

The term "vector" as used herein refers to any vehicle which delivers a nucleic acid into a cell or organism. Examples include plasmids, viral vectors, liposomes, or cationic lipids.

The term "wasting symptoms" as used herein is defined as a condition associated with consumption diseases.

An embodiment of the present invention is the growth hormone-releasing hormone analog having the amino acid sequence of SEQ ID NO:1 and all nucleotide sequences encoding same.

Additional embodiments of the present invention include: (1) a method for treating growth hormone-related deficiencies associated with the growth hormone pathway; (2) a method for treating growth hormone-related deficiencies associated with genetic disease; (3) a method to improve growth performance in an animal; (4) a method of treating an animal having a growth deficiency disease; (5) a method of increasing the efficiency of an animal used for food; (6) a method of treating in an animal wasting symptoms associated with bum, trauma, AIDS, or other consumption diseases; (7) a method for stimulating production of growth hormone in an animal at a level greater than that associated with normal growth; and (8) a method of enhancing growth in an animal. All of these methods include the step of introducing a plasmid vector into an animal, wherein said vector comprises a promoter; a nucleotide sequence encoding SEQ ID NO:1; and a 3' untranslated region operatively linked sequentially at appropriate distances for functional expression. In a specific embodiment these methods result in increasing, improving or enhancing growth, or they result in an increase of the production of growth hormone.

In a specific embodiment there is a method of treating growth hormone-related deficiencies associated with the growth hormone pathway in an animal comprising the step of introducing a therapeutically effective amount of a vector into an animal, said vector comprised of a promoter; a nucleotide sequence encoding SEQ ID NO: 1; and a 3' untranslated region operatively linked sequentially at appropriate distances for functional expression. A skilled artisan is aware that such deficiencies in the growth hormone pathway may affect it indirectly or directly, and the step affected may be upstream or downstream of GHRH action or function. In a specific embodiment in which a downstream step from GHRH action or function is affected, elevated levels of the GHRH analog of the present invention, originally administered in gene therapy form, overcomes this affected step.

In another specific embodiment there is a method of treating growth hormone-related deficiencies associated with genetic disease in an animal comprising the step of introducing a therapeutically effective amount of a vector into an animal, said vector comprised of a promoter; a nucleotide sequence encoding SEQ ID NO:1; and a 3' untranslated region operatively linked sequentially at appropriate distances for functional expression. The deficiency may be directly or indirectly caused by the genetic disease, and other phenotypes may also be present. Examples of genetic diseases include but are not limited to Creutzfeldt-Jakob disease, Cohen syndrome, aminopterin-methotrexate syndrome, Kabuki syndrome, Wolf-Hirschhorn syndrome, Russell-Silver syndrome, Miller-Dieker syndromes, Langerhans cell histiocytosis, Roberts syndrome, and 18q-syndrome.

In another embodiment there is a method of treating in an animal having a growth deficiency disease comprising the step of introducing a therapeutically effective amount of a vector into an animal, said vector comprised of a promoter; a nucleotide sequence encoding SEQ ID NO:1; and a 3' untranslated region operatively linked sequentially at appropriate distances for functional expression. The growth deficiency disease may be due to a genetic defect or due to a deficiency in the growth hormone pathway.

In another embodiment of the present invention there is a method of improving growth performance in an animal comprising the step of introducing an effective amount of a vector into cells of said animal, said vector comprised of a promoter; a nucleotide sequence encoding SEQ ID NO:1; and a 3' untranslated region operatively linked sequentially at appropriate distances for functional expression. The term "growth performance" as used herein is defined as the state or status of growth of an animal. The growth performance may be as a result of a genetic disease, a growth related deficiency, or exposure to a growth-affecting agent, either of the animal or of a parent of the animal. The method of improving growth performance in an animal in a specific embodiment comprises the method of increasing growth of the animal.

In an additional specific embodiment there is a method for stimulating production of growth hormone in an animal at a level greater than that associated with normal growth, said method comprising introducing into said animal an effective amount of a vector, said vector comprising a promoter; a nucleotide sequence encoding SEQ ID NO:1; and a 3' untranslated region operatively linked sequentially at appropriate distances for functional expression. A level greater than that associated with normal growth includes the basal, inherent growth of an animal with a growth-related deficiency or of an animal with growth levels similar to other similar animals in the population, including those with no growth-related deficiency.

In another embodiment there is a method of enhancing growth in an animal comprising introducing into said animal an effective amount of a vector, said vector comprising a promoter; a nucleotide sequence encoding SEQ ID NO:1; and a 3' untranslated region operatively linked sequentially at appropriate distances for functional expression. The animal whose growth is enhanced may or may not have a growth deficiency.

In an embodiment of the present invention there is a vector comprised of a promoter; a nucleotide sequence encoding SEQ ID NO:1; and a 3' untranslated region operatively linked sequentially at appropriate distances for functional expression. One skilled in the art recognizes that a variety of nucleotide sequences can be used to encode SEQ ID NO:1. The specific sequence to be used is partially determined on specific sequences to be modified and the experimental conditions determined by the skilled artisan for the specific use. As shown herein the skilled artisan can use a GHRH cDNA sequence for site-directed mutagenesis to create changes in the sequence to contain both the native or species-specific sequence and the desired amino acid substitutions for protease resistance, etc. Examples provided herein are directed toward how to alter the nucleotide sequence by methods such as site-directed mutagenesis to obtain the desired sequence. A skilled artisan is thus aware how to obtain a nucleotide sequence encoding SEQ ID NO:1 by utilizing, for example, SEQ ID NO:8 or a similar sequence from GenBank (see below) as a template to make alterations to it by site-directed mutagenesis or other known methods to obtain nucleotide sequence which encodes SEQ ID NO:1. The amino acid sequence of SEQ ID NO:1, which is encoded by multiple nucleotide sequences due to the wobble (third) position of each codon, could be easily created by a skilled artisan given the access to GenBank for sequence, the methods provided herein for site-directed mutagenesis, and a codon table for the genetic code, such as is found in any standard biochemistry or molecular biology textbook (e.g. Biochemistry $3^{rd}$ ed., L. Stryer; W.H. Freeman and Co., N.Y. (1988)).

In a preferred embodiment the promoter is a synthetic myogenic promoter and hGH 3' untranslated region is in the 3' untranslated region. In a specific embodiment of the present invention there is utilized a synthetic promoter, termed SPc5-12 (Li et al., 1999) (SEQ ID NO:6), which contains a proximal serum response element (SRE) from skeletal α-actin, multiple MEF-2 sites, MEF-1 sites, and TEF-1 binding sites, and greatly exceeds the transcriptional potencies of natural myogenic promoters. Other elements, including trans-acting factor binding sites and enhancers may be used in accordance with this embodiment of the invention. In an alternative embodiment, a natural myogenic promoter is utilized, and a skilled artisan is aware how to obtain such promoter sequences from databases including the National Center for Biotechnology Information (NCBI) GenBank database (http://www.ncbi.nlm.nih.gov/Genbank/GenbankSearch.html) or the NCBI PubMed site(http://www.ncbi.nlm.nih.gov/PubMed/). A skilled artisan is aware that these World Wide Web sites may be utilized to obtain sequences or relevant literature related to the present invention.

In a specific embodiment the hGH 3' untranslated region (SEQ ID NO:7) is utilized in a nucleic acid vector, such as a plasmid.

In a specific embodiment there is a method to increase growth hormone in an animal utilizing a vector comprising nucleotide sequence encoding SEQ ID NO:1. As described in the Examples, human GHRH cDNA (SEQ ID NO:8) is used as a template for site-directed mutagenesis to create changes of the sequence to contain both the native porcine sequence and the desired amino acid substitutions for protease resistance, etc. Thus, the Examples provide teachings herein regarding how to alter the nucleotide sequence by methods such as site-directed mutagenesis to obtain the desired sequence. A skilled artisan is thus aware how to obtain a nucleotide sequence encoding SEQ ID NO:1 by utilizing, for example, SEQ ID NO:8 or a similar sequence from GenBank (see supra) as a template to make alterations to it by site-directed mutagenesis or other known methods to obtain nucleotide sequence which encodes SEQ ID NO:1. The amino acid sequence of SEQ ID NO:1, which is encoded by multiple nucleotide sequences due to the wobble (third) position of each codon, could be easily created by a skilled artisan given the access to GenBank for sequence, the methods provided herein for site-directed mutagenesis, and a codon table for the genetic code, such as is found in any standard biochemistry or molecular biology textbook (e.g. *Biochemistry.* $3^{rd}$ ed., L. Stryer; W.H. Freeman and Co., N.Y. (1988)).

In specific embodiments said vector is selected from the group consisting of a plasmid, a viral vector, a liposome, or a cationic lipid. In further specific embodiments said vector is introduced into myogenic cells or muscle tissue. In a further specific embodiment said animal is a human, a pet animal, a work animal, or a food animal.

An additional embodiment is a pharmaceutical composition for stimulating the release of growth hormone in animals comprising SEQ ID NO:1 in a pharmaceutically acceptable carrier.

Another embodiment of the present invention is the nucleotide sequence encoding the growth hormone-releasing hormone having the amino acid sequence of SEQ ID NO:1.

In addition to the specific embodiment of introducing said construct into the animal via a plasmid vector, delivery systems for tranfection of nucleic acids into the animal or its cells known in the art may also be utilized. For example, other non-viral or viral methods may be utilized. A skilled artisan recognizes that a targeted system for non-viral forms of DNA or RNA requires four components: 1) the DNA or RNA of interest; 2) a moiety that recognizes and binds to a cell surface receptor or antigen; 3) a DNA binding moiety; and 4) a lytic moiety that enables the transport of the complex from the cell surface to the cytoplasm. Further, liposomes and cationic lipids can be used to deliver the therapeutic gene combinations to achieve the same effect. Potential viral vectors include expression vectors derived from viruses such as adenovirus, vaccinia virus, herpes virus, and bovine papilloma virus. In addition, episomal vectors may be employed. Other DNA vectors and transporter systems are known in the art.

One skilled in the art recognizes that expression vectors derived from various bacterial plasmids, retroviruses, adenovirus, herpes or from vaccinia viruses may be used for delivery of nucleotide sequences to a targeted organ, tissue or cell population. Methods which are well known to those skilled in the art can be used to construct recombinant vectors which will express the gene encoding the growth hormone releasing hormone analog. Transient expression may last for a month or more with a non-replicating vector and even longer if appropriate replication elements are a part of the vector system.

Nucleic Acids

1. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994, both incorporated herein by reference.

The term "expression vector" refers to a vector containing a nucleic acid sequence coding for at least part of a gene product capable of being transcribed. In a specific embodiment the nucleic acid sequence encodes part or all of GHRH. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

a. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous. In a specific embodiment the promoter is a synthetic myogenic promoter, such as is described in Li et al. (1999).

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996).

b. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

c. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

e. Polyadenylation Signals

In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

f. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

g. Selectable and Screenable Markers

In certain embodiments of the invention, the cells contain nucleic acid construct of the present invention, a cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

2. Host Cells

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5a, JM109, and KC8, as well as a number of commercially available bacterial hosts such as SURE® Competent Cells and SOLOPACKä Gold Cells (STRATAGENE®, La Jolla). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

3. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC®

2.0 from INVITROGEN® and BACPACK™ BACULOVIRUS EXPRESSION SYSTEM FROM CLONTECH®.

Other examples of expression systems include STRATAGENE®'s COMPLETE CONTROLäInducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Mutagenesis

Where employed, mutagenesis will be accomplished by a variety of standard, mutagenic procedures. Mutation is the process whereby changes occur in the quantity or structure of an organism. Mutation can involve modification of the nucleotide sequence of a single gene, blocks of genes or whole chromosome. Changes in single genes may be the consequence of point mutations which involve the removal, addition or substitution of a single nucleotide base within a DNA sequence, or they may be the consequence of changes involving the insertion or deletion of large numbers of nucleotides.

Mutations can arise spontaneously as a result of events such as errors in the fidelity of DNA replication or the movement of transposable genetic elements (transposons) within the genome. They also are induced following exposure to chemical or physical mutagens. Such mutation-inducing agents include ionizing radiations, ultraviolet light and a diverse array of chemical such as alkylating agents and polycyclic aromatic hydrocarbons all of which are capable of interacting either directly or indirectly (generally following some metabolic biotransformations) with nucleic acids. The DNA lesions induced by such environmental agents may lead to modifications of base sequence when the affected DNA is replicated or repaired and thus to a mutation. Mutation also can be site-directed through the use of particular targeting methods.

Site-Directed Mutagenesis

Structure-guided site-specific mutagenesis represents a powerful tool for the dissection and engineering of protein-ligand interactions (Wells, 1996, Braisted et al., 1996). The technique provides for the preparattion and testing of sequence variants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as *E. coli* polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as *E. coli* cells, and clones are selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multiresidue saturation mutagenesis are daunting (Warren et al., 1996, Brown et al., 1996; Zeng et al., 1996; Burton and Barbas, 1994; Yelton et al., 1995; Jackson et al., 1995; Short et al., 1995; Wong et al., 1996; Hilton et al., 1996). Hundreds, and possibly even thousands, of site specific mutants must be studied. However, improved techniques make production and rapid screening of mutants much more straightforward. See also, U.S. Pat. Nos. 5,798,208 and 5,830,650, for a description of "walk-through" mutagenesis.

Other methods of site-directed mutagenesis are disclosed in U.S. Pat. Nos. 5,220,007; 5,284,760; 5,354,670; 5,366,878; 5,389,514; 5,635,377; and 5,789,166.

In Vitro Scanning Mutagenesis

Random mutagenesis may be introduced using error prone PCR (Cadwell and Joyce, 1992). The rate of mutagenesis may be increased by performing PCR in multiple tubes with dilutions of templates.

One particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation (Cunningham et al., 1989).

In recent years, techniques for estimating the equilibrium constant for ligand binding using minuscule amounts of protein have been developed (Blackburn et al., 1991; U.S. Pat. Nos. 5,221,605 and 5,238,808). The ability to perform functional assays with small amounts of material can be exploited to develop highly efficient, in vitro methodologies for the saturation mutagenesis of antibodies. The inventors bypassed cloning steps by combining PCR mutagenesis with coupled in vitro transcription/translation for the high throughput generation of protein mutants. Here, the PCR products are used directly as the template for the in vitro transcription/translation of the mutant single chain antibodies. Because of the high efficiency with which all 19 amino acid substitutions can be generated and analyzed in this way, it is now possible to perform saturation mutagenesis on numerous residues of interest, a process that can be described as in vitro scanning saturation mutagenesis (Burks et al., 1997).

In vitro scanning saturation mutagenesis provides a rapid method for obtaining a large amount of structure-function information including: (i) identification of residues that modulate ligand binding specificity, (ii) a better understanding of ligand binding based on the identification of those amino acids that retain activity and those that abolish activity at a given location, (iii) an evaluation of the overall plasticity of an active site or protein subdomain, (iv) identification of amino acid substitutions that result in increased binding.

Dosage and Formulation

The composition (active ingredients; for example, SEQ ID NO:1 or nucleotide sequence encoding it or a vector with nucleotide sequence encoding SEQ ID NO:1) of this invention can be formulated and administered to affect a variety of growth deficiency states by any means that produces contact of the active ingredient with the agent's site of action in the body of an animal. The composition of the present invention is defined as a vector containing a nucleotide sequence encoding the compound of the invention, which is an amino acid sequence analog herein described. Said composition is administered in sufficient quantity to generate a therapeutically effective amount of said compound. A skilled artisan is aware that a sufficient vector amount is utilized to provide expression of a nucleotide sequence encoding SEQ ID NO:1 to therapeutically effective levels. One skilled in the art recognizes that the terms "administered" and "introduced" can be used interchangeably.

The composition can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice. Such pharmaceutical compositions can be used for therapeutic or diagnostic purposes in clinical medicine, both human and veterinary. For example, they are useful in the treatment of growth-related disorders such as hypopituitary dwarfism and diabetes resulting from abnormalities in growth hormone production. Furthermore they can also be used to stimulate the growth or enhance feed efficiency of animals raised for meat production, to enhance milk production, and stimulate egg production.

The dosage administered will be a therapeutically effective amount of active ingredient and will, of course, vary depending upon known factors such as the pharmacodynamic characteristics of the particular active ingredient and its mode and route of administration; type of animal; age of the recipient; sex of the recipient; health of the recipient; weight of the recipient; nature and extent of symptoms; kind of concurrent treatment; frequency of treatment; and the effect desired. Appropriate dosages of the vectors of the invention to be administered will vary somewhat depending on the individual subject and the condition being treated. The skilled worker will be able to determine appropriate dosages based on the known circulating levels of growth hormone associated with normal growth and the growth hormone releasing activity of the vector. As is well known in the art, treatment of growth-related disorders will necessitate varying dosages from individual to individual depending upon the degree of insufficiency of growth hormone production. The dosage employed to stimulate growth activity in livestock will be significantly higher (per kg of subject weight) than the dosages employed to restore normal growth in cases of growth hormone deficiencies such as pituitary dwarfism in humans.

Thus, there is provided in accordance with this invention a method of treating growth-related disorders characterized by insufficient production of growth hormone which comprises administering an amount of the analog of this invention sufficient to stimulate the production of growth hormone to levels associated with normal growth. Normal levels of growth hormone vary considerably among individuals and, for any given individual, levels of circulating growth hormone vary considerably during the course of a day.

There is also provided a method of increasing the growth rate of animals by administering an amount of the inventive GHRH analog sufficient to stimulate the production of growth hormone at a level greater than that associated with normal growth.

Gene Therapy Administration: Where appropriate, the gene therapy vectors can be formulated into preparations in solid, semisolid, liquid or gaseous forms in the ways known in the art for their respective route of administration. Means known in the art can be utilized to prevent release and absorption of the composition until it reaches the target organ or to ensure timed-release of the composition. A pharmaceutically acceptable form should be employed which does not ineffectuate the compositions of the present invention. In pharmaceutical dosage forms, the compositions can be used alone or in appropriate association, as well as in combination, with other pharmaceutically active compounds.

Accordingly, the pharmaceutical composition of the present invention may be delivered via various routes and to various sites in an animal body to achieve a particular effect (see, e.g., Rosenfeld et al. (1991); Rosenfeld et al., (1991a); Jaffe et al., 1992;).

One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

One skilled in the art recognizes that different methods of delivery may be utilized to administer a vector into a cell. Examples include: (1) methods utilizing physical means, such as electroporation (electricity), a gene gun (physical force) or applying large volumes of a liquid (pressure); and (2) methods wherein said vector is complexed to another entity, such as a liposome or transporter molecule.

Accordingly, the present invention provides a method of transferring a therapeutic gene to a host, which comprises administering the vector of the present invention, preferably as part of a composition, using any of the aforementioned routes of administration or alternative routes known to those skilled in the art and appropriate for a particular application. Effective gene transfer of a vector to a host cell in accordance with the present invention to a host cell can be monitored in terms of a therapeutic effect (e.g. alleviation of some symptom associated with the particular disease being treated) or, further, by evidence of the transferred gene or expression of the gene within the host (e.g., using the polymerase chain reaction in conjunction with sequencing, Northern or Southern hybridizations, or transcription assays to detect the nucleic acid in host cells, or using immunoblot analysis, antibody-mediated detection, mRNA or protein half-life studies, or particularized assays to detect protein or polypeptide encoded by the transferred nucleic acid, or impacted in level or function due to such transfer).

These methods described herein are by no means all-inclusive, and further methods to suit the specific application will be apparent to the ordinary skilled artisan. Moreover, the effective amount of the compositions can be further approximated through analogy to compounds known to exert the desired effect.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

The following examples are offered by way of example, and are not intended to limit the scope of the invention in any manner.

EXAMPLE 1

GHRH Super-active Analogs Increase GH Secretagogue Activity and Stability

GHRH has a relatively short half-life of about 12 minutes in the circulatory systems of both humans (Frohman et al., 1984) and pigs. By employing GHRH analogs that prolong its biological half-life and/or improve its GH secretagogue activity, enhanced GH secretion is achieved. GHRH mutants were generated by site directed mutagenesis. Gly15 was substituted for Ala15 to increase α-helical conformation and amphiphilic structure to decrease cleavage by trypsin-like enzymes (Su et al., 1991). GHRH analogs with Ala15 substitutions display a 4-5 fold greater affinity for the GHRH receptor (Campbell et al., 1991). To reduce loss of biological activity due to oxidation of the Met, with slightly more stable forms using molecules with a free COOH-terminus (Kubiak et al., 1989), substitution of Met27 and Ser28 for Leu27 and Asn28 was performed. Thus, a triple amino acid substitution mutant denoted as GHRH-15/27/28 was formed. Dipeptidyl peptidase IV is the prime serum GHRH degradative enzyme (Walter et al., 1980; Martin et al., 1993). Poorer dipeptidase substrates were created by taking GHRH15/27/28 and then by replacing Ile2 with Ala2 (GHRH-TI) or with Val2 (GHRH-TV), or by converting Tyr1 and Ala2 for His1 and Val2 (GHRH-HV (FIG. 1A); H1V2A15L27N28).

EXAMPLE 2

DNA Constructs

To test the biological potency of the mutated porcine GHRH cDNA sequences, plasmid vectors were engineered that were capable of directing the highest level of skeletal muscle-specific gene expression by a newly described synthetic muscle promoter, SPc5- 12, which contains a proximal serum response element frodm skeletal α-actin, multiple MEF-2 sites, multiple MEF-1 sites, and TEF-1 binding sites (Li et al., 1999). A 228-bp fragment of pGHRH, which encodes the 31 amino acid signal peptide and the entire mature peptide porcine GHRH (Tyr1-Gly40) and or the GHRH mutants, followed by the 3' untranslated region of hGH cDNA, were incorporated into myogenic GHRH expression vectors by methods well known in the art. The plasmid pSPc5-12 contains a 360 bp SacI/BamHI fragment of the SPc5-12 synthetic promoter (Li et al., 1999) in the SacI/BamHI sites of pSK-GHRH backbone (Draghia-Akli et al., 1997).

The wild type and mutated porcine GHRH cDNAs were obtained by site directed mutagenesis of human GHRH cDNA (SEQ ID NO:8) utilizing the kit Altered Sites II in vitro Mutagenesis System (Promega; Madison, Wis.). The human GHRH cDNA was subcloned as a BamHI-Hind III fragment into the corresponding sites of the pALTER Promega vector and mutagenesis was performed according to the manufacturer's directions. The porcine wild type cDNA was obtained from the human cDNA by changing the human amino acids 34 and 38 using the primer of SEQ ID:2: NO:5'-AGGCAGCAGGGAGAGAGGAACCAAGAG-CAAGGAGCATAATGACTGCAG-3'. The porcine HV mutations were made with the primer of SEQ ID NO:3: 5'-ACCCTCAGGATGCCGGCGGCACGTAGAT-GCCATCTTCACCAAC-3'. The porcine 15Ala mutation was made with the primer of SEQ ID NO:4: 5'-CGGAAG-GTGCTGGCCCAGCTGTCCGCC-3'. The porcine 27Leu28Asn mutation was made with the primer of SEQ ID NO:5: 5'-CTGCTCCCAGGACATCCTGAACAGGCAG-CAGGGAGAG-3'. Following mutagenesis the resulting clones were sequenced to confirm correctness and subsequently subcloned into the BamHI/Hind III sites of pSK-GHRH described in this Example by methods well known to those in the art.

A skilled artisan is aware that instead of SEQ ID NO:8, other GHRH sequences may be utilized, including those from *Mus musculus* (SEQ ID NO:9; GenBank Accession Number NM_010285); *Bos taurus* (SEQ ID NO:10; GenBank Accession Number AF168686 or SEQ ID NO:11; GenBank Accession Number BTU29611); *Equus caballus* (SEQ ID NO:12; GenBank Accession Number AF097587); *Rattus norvegicus* (SEQ ID NO:13; GenBank Accession Number RNU10156).

EXAMPLE 3

Cell Culture and Transfection

Experiments were performed in both pig anterior pituitary culture and primary chicken myoblast cultures with equal success. However, all figures demonstrate data generated with pig anterior pituitary cultures. Primary chicken myoblast cultures were obtained as follows. Chicken embronic tissue was harvested, dissected free of skin and cartilage and mechanically dissociated. The cell suspension was passed through cheesecloth and lens paper and plated at a density of $1\times10^8$ to $2\times10^8$/100 mm plastic culture dish. The cell populations which remained in suspension were plated at a density of $2\times10^6$ to $3\times10^6$ cells/collagen-coated 100 mm plastic dish and incubated at 37° C. in a 5% $CO_2$ environment. Cells were then incubated 24 hours prior to transfection at a density of $1.5\times10^6$/100 mm plate in Minimal Essential Medium (MEM) supplemented with 10% Heat Inactivated Horse Serum (HIHS), 5% chicken embryo extract (CEE) (Gibco BRL; Grand Island, N.Y.), and gentamycin. For further details see Draghia-Alli et al., 1997 and Bergsma et al., 1986. The pig anterior pituitary culture was obtained essentially as described (Tanner et al., 1990). Briefly, pituitary tissue was dissociated under enzymatic conditions, plated on plastic dishes for enough time to allow attachment. The cells were then rinsed and exposed to incubation media prior to experiments. For details see Tanner et al. (1990).

Cells were transfected with 4 mg of plasmid per 100 mm plate, using lipofectamine, according to the manufacturer instructions. After transfection, the medium was changed to MEM which contained 2% HIHS and 2% CEE to allow the cells to differentiate. Media and cells were harvested 72 hours post-differentiation. The efficiency of transfection was estimated by β-galactosidase histochemistry of control plates to be 10%. One day before harvesting, cells were washed twice in Hank's Balanced Salt Solution (HBSS) and the media changed to MEM, 0.1% bovine serum albumin. Conditioned media was treated by adding 0.25 volume of 1% trifluoroacetic acid and 1 mM phenylmethylsulfonylflouride, frozen at −80° C., lyophilized, purified on C-18 Sep-Columns (Peninsula Laboratories, Belmont, Calif.), relyophilized and used in radioimmunoassays or resuspended in media conditioned for primary pig anterior pituitary culture.

EXAMPLE 4

GHRH Super-Active Analogs Increase GH Secretagogue Activity and Stability

Skeletal myoblasts were transfected as in Example 3 with each construct and GHRH moieties purified from conditioned culture media cells were assayed for growth hormone secretion in pig anterior pituitary cell cultures. As shown in FIG. 1B, media collected after 24 hours and quantitated by porcine specific GH-radioimmunoassays showed that modest gains in GH secretion amounting to about 20% to 50% for the modified GHRH species (GH15/27/28; GHRH-TI; GHRH-TV) overwild-type pGHRH. Only one of the four mutants, GHRH-HV, had a substantial increase in GH secretagogue activity in which pGH levels rose from baseline values of 200 ng/ml up to 1600 ng/ml (FIG. 1B).

EXAMPLE 5

Plasma Incubation of HV-GHRH Molecule

Pooled porcine plasma was collected from control pigs, and stored at −80° C. Chemically synthesized HV-GHRH was prepared by peptide synthesis. The porcine plasma was thawed and centrifuged, placed at 37° C. and allowed to equilibrate. GHRH mutant was dissolved into plasma sample to a final concentration of 100μg/ml. Immediately after the addition of the GHRH mutant, and 15, 30, 60, 120 and 240 minutes later, 1 ml of plasma was withdrawn and acidified with 1 ml of 1MTFA. Acidified plasma was purified on C18 affinity SEP-Pak columns, lyophilized and analyzed by HPLC, using a Walters 600 multi-system delivery system, a Walters intelligent sample processor, type 717 and a Walters spectromonitor 490 (Walters Associates, Millipore Corp., Milford, Mass.). The detection was performed at 214 nm. The percent of peptide degraded at these time points was measured by integrated peak measurements.

Stability of wild type GHRH and the analog GHRH-HV was then tested in porcine plasma, by incubation of GHRH peptides, followed by solid phase extraction, and HPLC, analysis. As shown in FIG. 1C, 95% of the wildtype GHRH (1–44)$NH_2$ was degraded within 60 minutes of incubation in plasma. In contrast, incubation of GHRH-HV in pig plasma showed that at least 75% of the polypeptides was protected against enzymatic cleavage, during 4 to 6 hours of incubation. Thus, under identical conditions, a major portion of GHRH-HV remained intact, while the wild-type GHRH is completely degraded, indicating a considerable increase in stability for GHRH-HV to serum proteases (FIG. 1C).

EXAMPLE 6

Animal Studies

Three groups of five, 3–4 weeks old hybrid cross barrows (Yorkshire, Landrace, Hampshire and Duroc) were used in the GHRH studies. The animals were individually housed with ad lib access to water, and 6% of their body weight diet (24% protein pig meal, Producers Cooperative Association, Bryan, Tex.). The animals were weighed every other day, at 8:30 am, and the feed was subsequently added. Animals were maintained in accordance with NIH Guide, USDA and Animal Welfare Act guidelines.

EXAMPLE 7

Intramuscular Injection of Plasmid DNA in Porcine

Endotoxin-free plasmid (Qiagen Inc., Chatsworth, Calif.) preparations of pSPc5-12-HV-GHRH, pSPc5-12-wt-GHRH and pSPc5-12bgal were diluted in PBS (pH 7.4) to 1 mg/ml. The animals were assigned equally to one of the treatments. The pigs were anesthetized with isoflurane (concentration of 2–6 % for induction and 1–3 % for maintenance). Jugular catheters were implanted by surgical procedure to draw blood from the animals at day 3, 7, 14, 21, 28, 45 and 65 post-injection. While anesthetized, 10 mg of plasmid was injected directly into the semitendinosus muscle of pigs. Two minutes after injection, the injected muscle was placed in between a set of calipers and electroporated using optimized conditions of 200V/cm with 4 pulses of 60 milliseconds (Aihara et al., 1998). At 65 days post-injection, animals were killed and internal organs and injected muscle collected, weighed, frozen in liquid nitrogen, and stored at −80° C. Carcass' were weighed and analyzed by neutron activation. Back fat was measured.

EXAMPLE 8

Muscle Injection of pSP-HV-GHRH Increases Porcine GHRH; GH and IGF-I Serum Levels Over Two Months The ability of the optimized protease resistant pSP-HV-GHRH vector to facilitate long term expression of GHRH and stimulate GH and IGF-I secreted levels was determined. Schematic maps of pSP-HV-GHRH, as well as the wild-type construct, pSP-wt-GHRH, as a wild-type control, and an synthetic myogenic promoter *E. coli*. β-galactosidase expression vector, pSP-bgal, as the placebo control, is shown in FIG. 2A. Three-week-old castrated male-pigs were anesthetized and a jugular vein catheter was inserted to allow collection of blood samples with no discomfort for the animals. Plasmid expression vector DNA (10 mg of DNA of pGHRH-HV; pSP-GHRH; or pSP-bgal) was injected directly into semitendinosus muscle, which was then electroporated (See Example 7).

EXAMPLE 9

Porcine GHRH, GH and IGF-1 Measurements

Porcine GHRH was measured by a heterologous human assay system (Peninsula Laboratories, Belmont, Calif.). Sensitivity of the assay is 1 pg/tube. Porcine GH in plasma was measured with a specific double antibody procedure RIA (The Pennsylvania State University). The sensitivity of the assay is 4 ng/tube. Porcine IGF-1 was measured by heterologous human assay (Diagnostic System Lab., Webster, Tex.). Data are analyzed using Microsoft Excel statistics analysis package. Values shown in the figures are the mean±s.e.m. Specific p values were obtained by comparison using Students t test. A $p<0.05$ is set as the level of statistical significance. In pigs injected in semitendinosus muscle with pSP-GHRH-HV, GHRH levels was increased at 7 days post-injection (FIG. 2B), and were 150% above the control levels at 14 days (652.4±77 pg/ml versus 419.6±13 pg/ml). pSP-GHRH-HV expression activity reached a plateau by 60 days that was about 2 to 3 fold greater levels than the placebo injected control values. The absolute quantity of serum GHRH, corrected for increased body weight between day 0 and day 60 (blood volume accounts for 8% of total body weight), secreted by the pSP-GHRH-HV injected pigs was 3 times greater than the placebo injected control values (1426.49±10.47 ng versus 266.84±25.45 ng) (FIG. 2C). The wild-type pSP-GHRH injected animals, which had been injected in semitendinosus muscle, showed only a modest increase in their GHRH levels starting with 45 days post-injection, but a 2-fold increase by 60 days post-injection (779.36 ng), at levels sufficient to elicit a biological effect.

Young animals have very high levels of GH that gradually decrease with age. Blood samples, taken every 15 minutes over a 24-hour period after the 7 and 14 days following the initial injections, were assayed for pGH levels which were extrapolated for the total change in pGH content. The pGHRH-HV injected pigs (FIG. 2D) showed an increase in their GH content evident at day 7 post-injection (delta variation HV=+1.52, wt=−0.73 versus control=−3.2 ng/ml) and 14 days post-injection (delta variation HV=+1.09, wt=− control=−6.88 ng/ml).

Figure 2E:
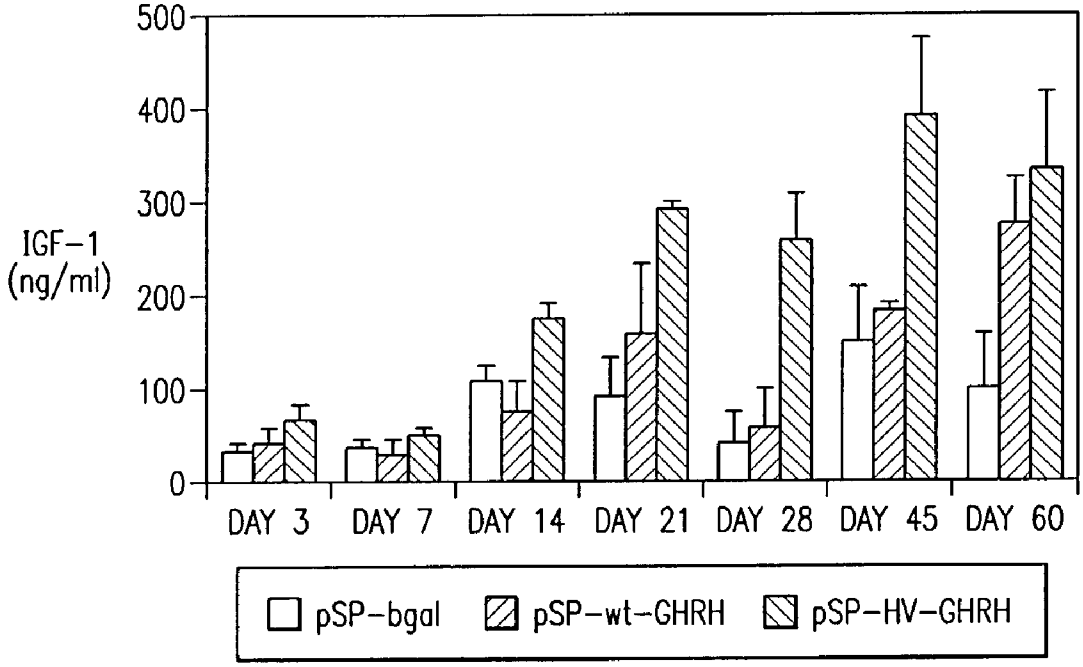

Another indication of increased systemic levels of GH would be elevated levels of IGF-I. Serum porcine IGF-1 levels started to rise in pSP-GHRH-HV injected pigs at about 3 days post-injection (FIG. 2E). At 21 days, these animals averaged about a 3-fold increase in serum IGF-1 levels, which was maintained over 60 days ($p<0.03$). In comparison, pigs injected with the wild-type pSP-GHRH expression vector had only a 40% increase in their circulating IGF-1 levels ($p=0.39$), as shown in FIG. 2E.

EXAMPLE 10

Myogenic GHRH Expression Vectors Enhance Pig Growth

Figure 3A:
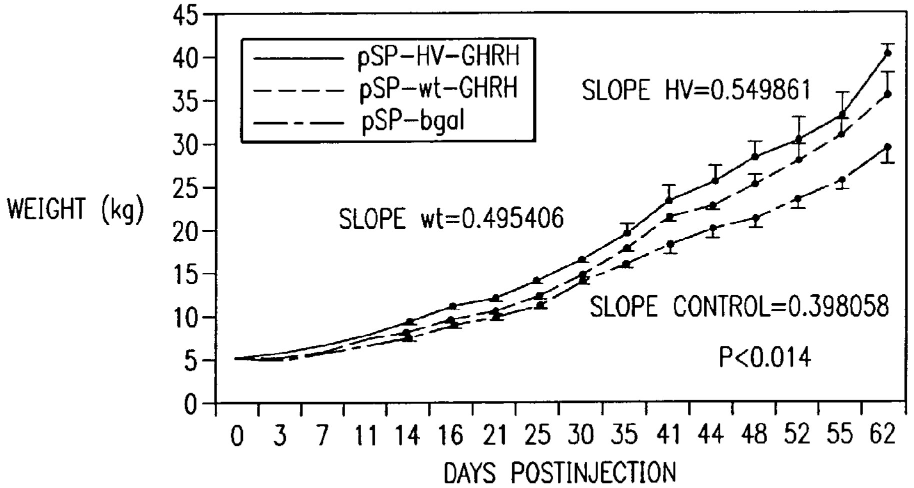
FIG. 3A through FIG. 3C demonstrate the effect of myogenic GHRH expression vectors on pig growth.
Figure 3B:
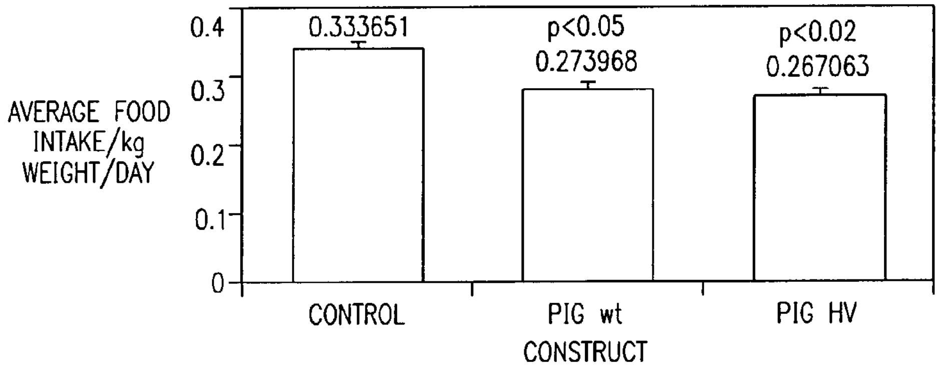
Figure 3C:
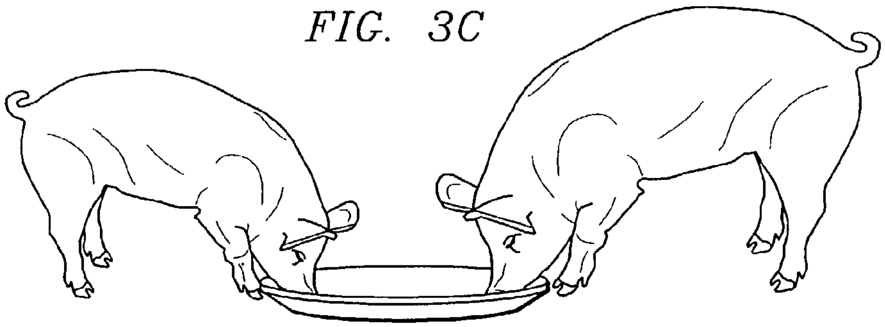

Porcine GH secreted into the systemic circulation after intramuscular injection of myogenic pSP-GHRH expression vectors augments growth over 65 days in castrated young male pigs. Body composition measurements were performed either in vivo, at day 30 and 65 post-injection (densitometry, K40) or post-mortem (organ, carcass, body fat, direct dissection followed by neutron activation chamber). Wild-type pSP-GHRH injected animals were on average 21.5% heavier than the placebo controls (37.125 kg vs. 29.375 kg), while the pSP-GHRH-HV injected pigs were 37.8% heavier (41.775 kg; $p=0.014$), as shown in FIG. 3A. Feed efficiency was also improved by 20% in pigs injected with GHRH constructs when compared with controls (0.267 kg of food/day for each kg weight gain in pSP-HV-GHRH, and 0.274 kg in pSP-wt-GHRH, versus 0.334 kg in pSP-bgal injected pigs (FIG. 3B). Body composition studies by densitometry, K40 potassium chamber and neutron activation chamber showed a proportional increase of all body components in GHRH injected animals, with no signs of organomegaly, relative proportion of body fat and associated pathology. A photograph of a placebo injected control pig and a pSP-GHRH-HV injected pig after 45 days is shown in FIG. 3C.

The metabolic profile of pSP-HV-GHRH injected pigs shown in Table I connotes a significant decrease in serum urea level, pSP-GHRH and pSP-GHRH-HV, respectively (9±0.9 mg/dl in controls, 8.3±1 mg/dl and 6.875±0.5 mg/dl in injected pigs) ($p=0.006$), indicating decreased amino acid catabolism. Serum glucose level was similar between the controls and the plasmid GHRH injected pigs (99.2±4.8 mg/dl in control pigs, 104.8±6.9 mg/dl in pSP-GHRH-HV injected pigs and 97.5±8 mg/dl in wildtype pSP-GHRH injected animals ($p=0.263$). No other metabolic changes were found.

TABLE 1

The metabolic profile of GHRH injected pigs and controls (values in mg/ml).

| | glucose | urea | creatinine | total protein |
|---|---|---|---|---|
| Control | 99.2 ± 4.8 | 9 ± 0.9 | 0.82 ± 0.06 | 4.6 ± 0.22 |
| pSP-wt-GHRH | 97.5 ± 8 | 8.3 ± 1 | 0.83 ± 0.056 | 4.76 ± 0.35 |
| pSP-HV-GHRH | 104.8 ± 6.9 | 6.875 ± 0.5 | 0.78 ± 0.04 | 4.88 ± 0.23 |

EXAMPLE 11

Experiments with Different Levels of pSP-HV-GHRH

Figure 4:
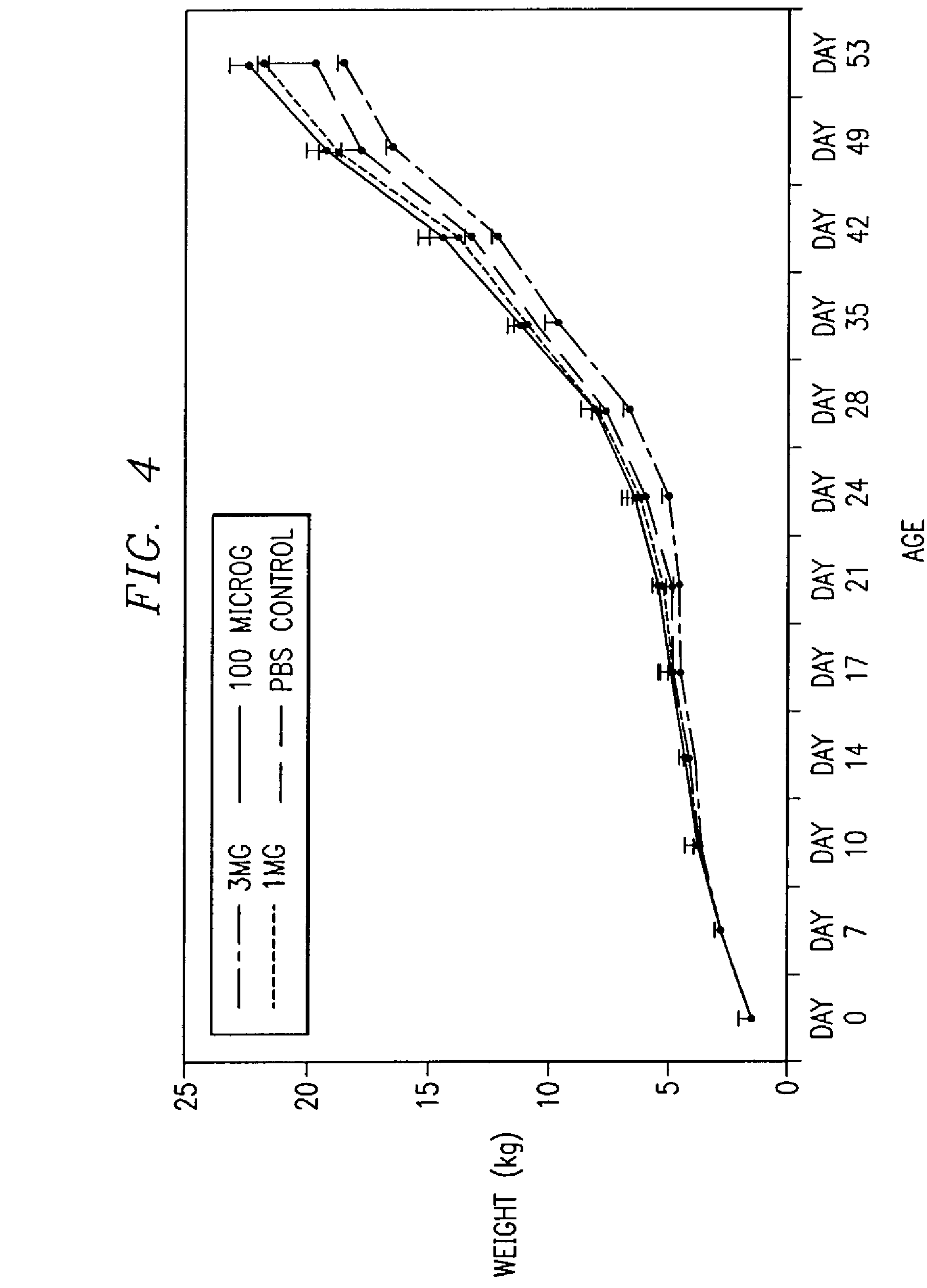
FIG. 4 demonstrates the effect of injection of different amounts of pSP-GHRH-HV on 10 day-old piglets.
Figure 5:
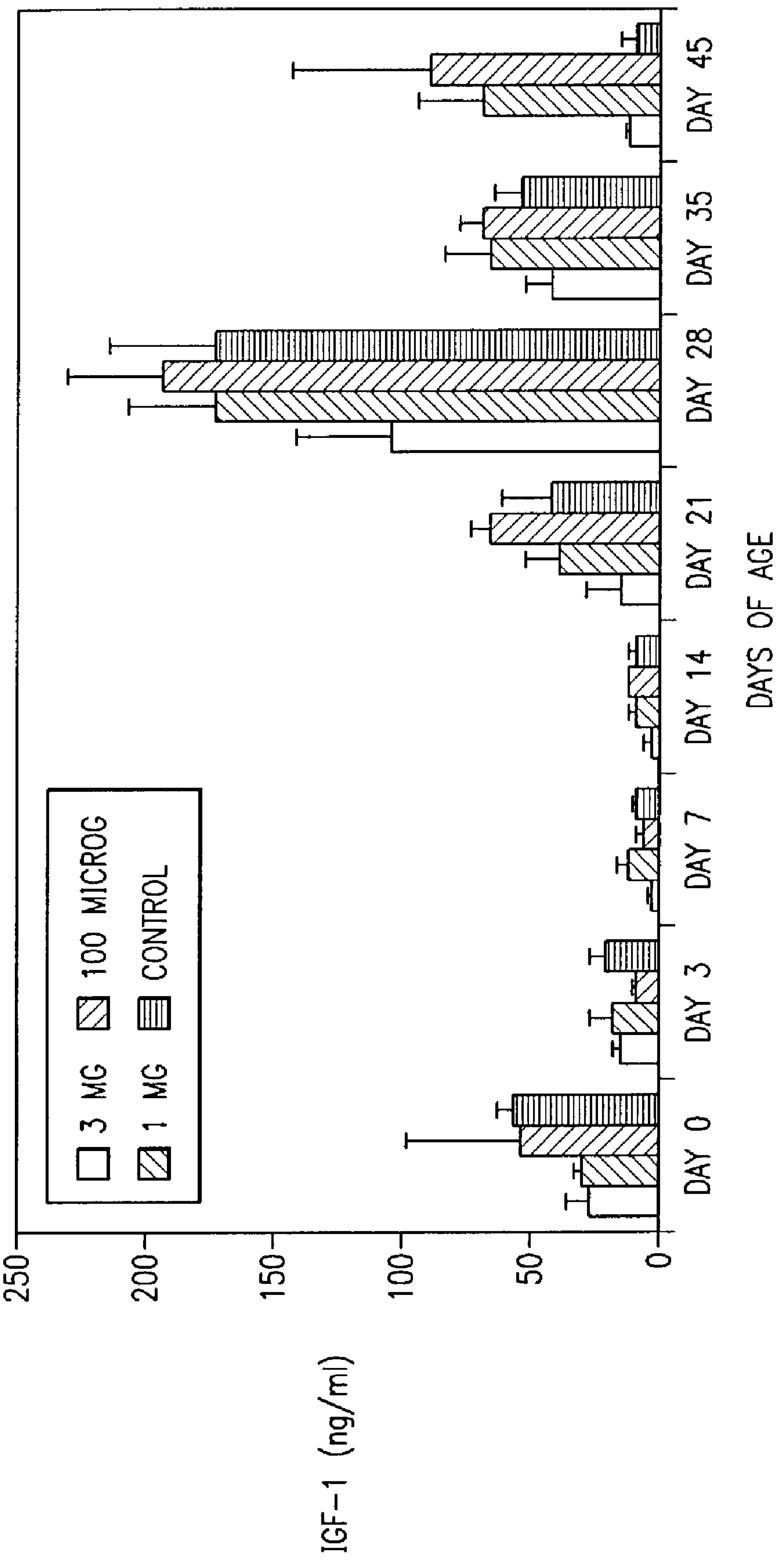
FIG. 5 shows the effect of injection of different amounts of pSP-GHRH-HV on IGF-I levels in 10 day-old piglets.

To further investigate the effects of pSP-HV-GHRH on the growth in piglets, groups of 2 piglets were injected at 10 days after birth with pSP-HV-GHRH (3 mg, 1 mg, 100 microg). As shown in FIG. 4, the group injected with 100 micrograms of the plasmid presented the best growth curve, with significantly statistically differences to controls after 50 days of age. One animal in the group injected with 3 mg developed antibodies and showed a significantly decreased growth pattern.

Also, groups of 2 piglets were injected with the indicated doses of pSP-HV-GHRH 10 days afterbirth. IGF-I values started to rise 10 days post-injection, and at 35 days post-injection pigs injected with 100 micrograms plasmid averaged 10.62 fold higher IGF-I than the controls. Pigs injected with 1 mg averaged 7.94 fold over the controls, and pigs injected with 3 mg averaged 1.16 fold over control values.

Thus, in a specific embodiment lower dosages of pSP-HV-GHRH are injected. In a specific embodiment about 100 micrograms (0.1 milligrams) of the plasmid is utilized. In another specific embodiment about 200-300 micrograms are injected.

EXAMPLE 12

Age Comparisons with pSP-HV-GHRH

Figure 6:
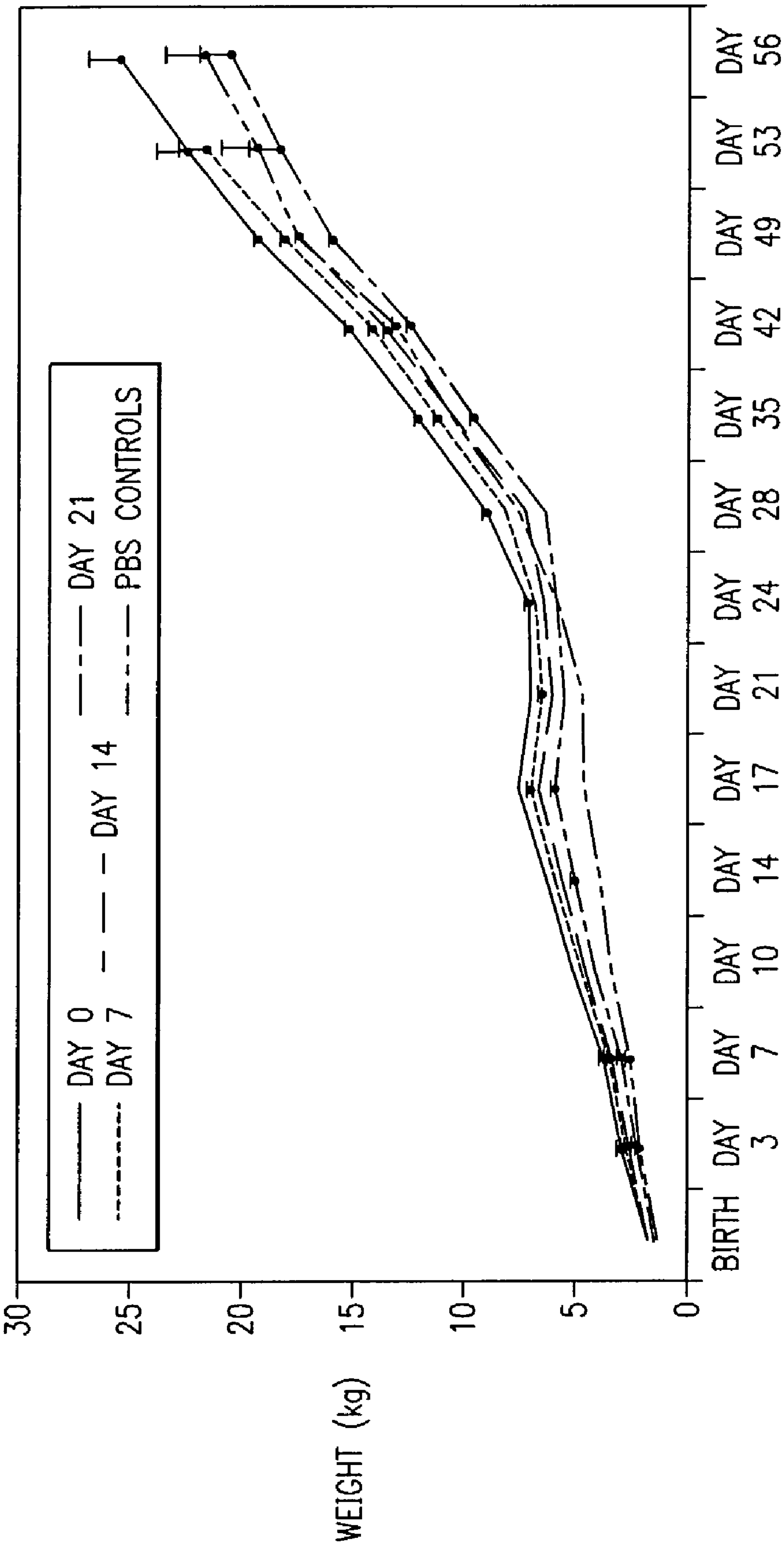
FIG. 6 illustrates a time course for pSP-GHRH-HV plasmid injection into piglets.

To optimize the age of piglets for pSP-HV-GHRH injection, groups of 2 piglets were injected starting at birth with 2 mg pSP-HV-GHRH. As shown in FIG. 6, the group injected 14 days after birth presented the best growth curve, with significantly statistically differences compared to the control at every time point. One animal in the group injected at 21 days developed antibodies and showed a significantly decreased growth pattern. It is possible that there is insulin resistance if treated too early (i.e. <about 10–14 days of age). In a specific embodiment the therapy is most effective when natural GH and IGF-I levels are the lowest (about 10–14 days of life), and may be counterproductive when GHRH levels are normally high.

EXAMPLE 13

Summary

In summary, an optimal time point for injection is 14 days after birth (an average 8 pounds heavier than the controls ($p<0.04$) at 40 days post-injection). A preferred dosage for injection is 100 micrograms plasmid in 2–5 ml volume (an average 6 pounds heavier than the controls ($p<0.02$) at 40 days post-injection). Hormonal and biochemical constants are normal (IGF-I, IGF-BP3, insulin, urea, glucose, total proteins, creatinine) in the offspring of sow 1 (time course) and sow 3 (dose curve) and in correlation with weight increase, with no deleterious side effects. Body composition studies from the previous experiment showed that HV-GHRH determined a uniform increase of all body compartments (body composition similar to the controls but bigger), while wt-GHRH determined an increase in lean body mass and a decrease in fat.

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

REFERENCES CITED

U.S. Patent Documents

U.S. Pat. No. 5,847,066 issued on Dec. 8, 1998 with Coy et al. listed as inventors.
U.S. Pat. No. 5,846,936 issued on Dec. 8, 1998 with Felix et al. listed as inventors.
U.S. Pat. No. 5,792,747 issued on Aug. 11, 1998 with Schally et al. listed as inventors.
U.S. Pat. No. 5,776,901 issued on Jul. 7, 1998 with Bowers et al. listed as inventors.
U.S. Pat. No. 5,756,264 issued on May 26, 1998 with Schwartz et al. listed as inventors.
U.S. Pat. No. 5,696,089 issued on Dec. 9, 1997 with Felix et al. listed as inventors.
U.S. Pat. No. 5,486,505 issued on Jan. 23, 1996 with Bowers et al. listed as inventors.
U.S. Pat. No. 5,137,872 issued on Aug. 11, 1992 with Seely et al. listed as inventors.
U.S. Pat. No. 5,084,442 issued on Jan. 28,1992 with Felix et al. listed as inventors.
U.S. Pat. No. 5,036,045 issued on Jul. 30, 1991 with Thorner listed as the inventor.
U.S. Pat. No. 5,023,322 issued on Jun. 11, 1991 with Kovacs et al. listed as inventors.
U.S. Pat. No. 4,839,344 issued on Jun. 13, 1989 with Bowers et al. listed as inventors.
U.S. Pat. No. 4,410,512 issued on Oct. 18, 1983 with Bowers et al. listed as inventors.
U.S. Pat. No. RE33,699 issued on Sep. 24, 1991 with Drengler listed as the inventor.
U.S. Pat. No. 4,833,166 issued on May 23, 1989 with Grosvenor et al. listed as inventors.
U.S. Pat. No. 4,228,158 issued on Oct. 14, 1980 with Momany et al. listed as inventors.
U.S. Pat. No. 4,228,156 issued on Oct. 14, 1980 with Momany et al. listed as inventors.
U.S. Pat. No. 4,226,857 issued on Oct. 7, 1980 with Momany et al. listed as inventors.
U.S. Pat. No. 4,224,316 issued on Sep. 23, 1980 with Momany et al. listed as inventors.
U.S. Pat. No. 4,223,021 issued on Sep. 16, 1980 with Momany et al. listed as inventors.
U.S. Pat. No. 4,223,020 issued on Sep. 16, 1980 with Momany et al. listed as inventors.
U.S. Pat. No. 4,223,019 issued on Sep. 16, 1980 with Momany et al. listed as inventors.

Publications

Aihara, H. & Miyazaki, *J. Nat. Biotechnol.* 16, 867–870 (1998).
Albanese, A. and R. Stanhope. 1997. GH treatment induces sustained catch-up growth in children with intrauterine growth retardation: 7-year results. *Horm. Res.* 48:173–177.
Allen, D. B., A. C. Rundle, D. A. Graves, and S. L. Blethen. 1997. Risk of leukemia in children treated with human growth hormone: review and reanalysis. *J. Pediatr.* 131: S32–S36
Azcona, C., A. Albanese, P. Bareille, and R. Stanhope. 1998. Growth hormone treatment in growth hormone-sufficient and -insufficient children with intrauterine growth retardation/Russell-Silver syndrome. *Horm. Res.* 50:22–27.
Bartke, A. 1998. Growth hormone and aging. *Endocrine* 8:103–108.
Benfield, M. R. and E. C. Kohaut. 1997. Growth hormone is safe in children after renal transplantation. *J. Pediatr.* 131:S28–S31
Bercu, B. B., R. F. Walker. 1997. Growth hormone secretagogues in children with altered growth. *Acta Paediatrica* 86:102–106.
Bergsma, D. J., Grichnik, J. M., Gossett, L. M. & Schwartz, R. J. *Mol. Cell. Biol.* 6,2462–2475 (1986).
Blethen, S. L. and A. C. Rundle. 1996. Slipped capital femoral epiphysis in children treated with growth hormone. A summary of the National Cooperative Growth Study experience. *Horm. Res.* 46:113–116.
Campbell, R. M., Y. Lee, J. Rivier, E. P. Heimer, A. M. Felix, and T. F. Mowles. 1991. GRF analogs and fragments: correlation between receptor binding, activity and structure. *Peptides* 12:569–574.
Corpas, E., S. M. Harman, and M. R. Blackman. 1993. Human growth hormone and human aging. *Endocrine Reviews* 14:20–39.
Corpas, E., S. M. Harman, M. A. Pineyro, R. Roberson, and M. R. Blackman. 1993. Continuous subcutaneous infusions of growth hormone (GH) releasing hormone 1–44 for 14 days increase GH and insulin-like growth factor-I levels in old men. *Journal of Clinical Endocrinology & Metabolism* 76:134–138.

Davis, H. L., Whalen, R. G. & Demeneix, B. A. *Hum. Gene Ther.* 4, 151–159 (1993).

D'Costa, A. P., R. L. Ingram, J. E. Lenham, and W. E. Sonntag. 1993. The regulation and mechanisms of action of growth hormone and insulin-like growth factor 1 during normal aging. *J. Reprod. Fert.—Supp.* 46:87–98.

Draghia-Akli, R., Li, X. G., Schwartz, R. J., et al. *Nat. Biotechnol.* 15,1285–1289 (1997).

Eicher, E. M. and W. G. Beamer. 1976. Inherited ateliotic dwarfism in mice. Characteristics of the mutation, little, on chromosome 6. *J. Hered.* 67:87–91.

Erling, A. 1999. Methodological considerations in the assessment of health-related quality of life in children. *Acta Paediatrica Scandin.—Supp.* 428:106–107. 0803–5326.

Esch, F. S., P. Bohlen, N. C. Ling, P. E. Brazeau, W. B. Wehrenberg, M. O. Thorner, M. J. Cronin, and R. Guillemin. 1982. Characterization of a 40 residue peptide from a human pancreatic tumor with growth hormone releasing activity. *Biochemical & Biophysical Research Communications* 109:152–158.

Frohman, M. A., T. R. Downs, P. Chomczynski, and L. A. Frohman. 1989. Cloning and characterization of mouse growth hormone-releasing hormone (GRH) complementary DNA: increased GRH messenger RNA levels in the growth hormone-deficient lit/lit mouse. *Mol. Endocrinol.* 3:1529–1536.

Frohman, L. A., J. L. Thominet, C. B. Webb, M. L. Vance, H. Uderman, J. Rivier, W. Vale, and M. O. Thorner. 1984. Metabolic clearance and plasma disappearance rates of human pancreatic tumor growth hormone releasing factor in man. *J. Clin. Invest.* 73:1304–1311.

Gesundheit, N. and J. K. Alexander. 1995. Endocrine Therapy with Recombinant Hormones and Growth Factors. In Molecular Endocrinology: Basic Concepts and Clinical Correlations. B. D. Weintraub, editor. Raven Press, Ltd., N.Y. 491–507.

Heptulla, R. A., S. D. Boulware, S. Caprio, D. Silver, R. S. Sherwin, and W. V. Tamborlane. 1997. Decreased insulin sensitivity and compensatory hyperinsulinemia after hormone treatment in children with short stature. *J. Clin. Endocrinol. Metab.* 82:3234–3238.

Iranmanesh, A., G. Lizarralde, and J. D. Veldhuis. 1991. Age and relative adiposity are specific negative determinants of the frequency and amplitude of growth hormone (GH) secretory bursts and the half-life of endogenous GH in healthy men. *Journal of Clinical Endocrinology & Metabolism* 73:1081–1088.

Jacobs, P. A., P. R. Betts, A. E. Cockwell, J. A. Crolla, M. J. Mackenzie, D. O. Robinson, and S. A. Youings. 1990. A cytogenetic and molecular reappraisal of a series of patients with Turner's syndrome. *Ann. Hum. Genet.* 54:209–223.

Jaffe, H. A., C. Danel, G. Longenecker, M. Metzger, Y. Setoguchi, M. A. Rosenfeld, T. W. Gant, S. S. Thorgeirsson, L. D. Stratford-Perricaudet, M. Perricaudet, A. Pavirani, J.-P. Lecocq and R. G. Crystal. 1992. Adenovirus-mediated in vivo gene transfer and expression in normal rat liver. *Nat Genet* 1(5):372–8.

Key, L. L. J. and A. J. Gross. 1996. Response to growth hormone in children with chondrodysplasia. *J. Pediatr.* 128:S14–S17

Kubiak, T. M., C. R. Kelly, and L. F. Krabill. 1989. In vitro metabolic degradation of a bovine growth hormone-releasing factor analog Leu27-bGRF(1–29)NH2 in bovine and porcine plasma. Correlation with plasma dipeptidylpeptidase activity. *Drug Metabolism & Disposition* 17:393–397.

Li, X., Eastman, E. M., Schwartz, R. J., & Draghia-Akli, R. *Nat. Biotechnol.* 17. 3, 241–245 (1999).

Martin, R. A., D. L. Cleary, D. M. Guido, H. A. Zurcher-Neely, and T. M. Kubiak. 1993. Dipeptidyl peptidase IV (DPP-IV) from pig kidney cleaves analogs of bovine growth hormone-releasing factor (bGRF) modified at position 2 with Ser, Thr or Val. Extended DPP-IV substrate specificity? *Biochimica et Biophysica Acta* 1164: 252–260.

Monti, L. D., P. Brambilla, A. Caumo, F. Magni, S. Omati, G. Nizzoli, B. di Natale, M. Galli-Kienle, C. Cobelli, G. Chiumello, and G. Pozza. 1997. Glucose turnover and insulin clearance after growth hormone treatment in girls with Turner's syndrome. *Metabolism* 46:1482–1488.

Muramatsu, T., Nakamura, A. & Park, H. M. *Int. J. Mol. Med.* 1, 55–62 (1998).

Parks, J. S., R. W. Pfaffle, M. R. Brown, H. Abdul-Latif, and L. R. Meacham. 1995. Growth Hormone Deficiency. In Molecular Endocrinology: Basic Concepts and Clinical Correlations. B. D. Weintraub, editor. Raven Press, Ltd., New York. 473–490.

Rosenbaum, P. L. and S. Saigal. 1996. Measuring health-related quality of life in pediatric populations: conceptual issues. In Quality of life and pharmacoeconomics in clinical trials. B. Spilker, editor. Lippincott-Raven Publishers, Philadelphia.

Rosenfeld, M. A., K Yoshimura, L. E. Stier, B. C. Trapnell, L. D. Stratford-Perricaudet, M. Perricaudet, W. Dalemans, S. Jallat, A. Mercenier, A. Pavirani, J. P. Lecocq, W. B. Guggino, R. G. Crystal. 1991. In vivo transfer of the human cystic fibrosis gene to the respiratory epithelium. *Clinical Research* 39 (2), 311A.

Rosenfeld, M. A., W Siegfried, K Yoshimura, K Yoneyama, M Fukayama, L E Stier, P K Paakko, P Gilardi, L D Stratford-Perricaudet, M Perricaudet, S. Jallat, A. Pavirani, J.-P. Lecocq, and R. G. Crystal. 1991. Adenovirus-mediated transfer of a recombinant alpha 1-antitrypsin gene to the lung epithelium in vivo. *Science* 252(5004): 431–4.

Savage, M. O., R. M. Beattie, C. Camacho-Hubner, J. A. Walker-Smith, and I. R. Sanderson. 1999. Growth in Crohn's disease. *Acta Paediatrica Scandin—Supp.* 428: 89–92.

Scanlon, M. F., B. G. Issa, and C. Dieguez. 1996. Regulation of Growth Hormone Secretion. *Hormone Research* 46:149–154.

Shalet, S. M., B. M. Brennan, and R. E. Reddingius. 1997. Growth hormone therapy and malignancy. *Horm. Res.* 48 Suppl 4:29–32:29–32.

Skuse, D. H., K. Elgar, and E. Morris. 1999. Quality of life in Turner syndrome is related to chromosomal constitution: implication for genetic counseling and management. *Acta Paediatrica Scandin.—Supp.* 428:110–113.

Sohmiya, M., K. Ishikawa, and Y. Kato. 1998. Stimulation of erythropoietin secretion by continuous subcutaneous infusion of recombinant human GH in anemic patients with chronic renal failure. *Eur. J. Endocrinol.* 138:302–306.

Su, C. M., L. R. Jensen, E. P. Heimer, A. M. Felix, Y. C. Pan, and T. F. Mowles. 1991. In vitro stability of growth hormone releasing factor (GRF) analogs in porcine plasma. *Hormone & Metabolic Research* 23:15–21.

Tanaka, H., T. Kubo, T. Yamate, T. Ono, S. Kanzaki, and Y. Seino. 1998. Effect of growth hormone therapy in children with achondroplasia: growth pattern, hypothalamic-pituitary function, and genotype. *Eur. J. Endocrinol.* 138:275–280.

Tanner, J. W., Davis, S. K., McArthur, N. H., French, J. T. & Welsh, T. H., Jr. *J. Endocrinol.* 125, 109–115 (1990).

Thorner, M. O., L. A. Frohman, D. A. Leong, J. Thominet, T. Downs, P. Hellmann, J. Chitwood, J. M. Vaughan, and W. Vale. 1984. Extrahypothalamic growth-hormone-releasing factor (GRF) secretion is a rare cause of acromegaly: plasma GRF levels in 177 acromegalic patients. *Journal of Clinical Endocrinology & Metabolism* 59:846–849.

Tripathy, S. K., Svensson, E. C., Black, H. B., et al. *Proc. Natl. Acad. Sci. USA* 93, 10876–10880 (1996).

Walter, R., W. H. Simmons, and T. Yoshimoto. 1980. Proline specific endo- and exopeptidases. *Mol. Cell Biochem.* 30:111–127.

Watkins, S. L. 1996. Bone disease in patients receiving growth hormone. *Kidney Int. Suppl.* 53:S126–7: S126–S127

One skilled in the art readily appreciates that the patent invention is well adapted to carry out the objectives and obtain the ends and advantages mentioned as well as those inherent therein. Growth hormone, growth hormone releasing hormone, analogs, plasmids, vectors, pharmaceutical compositions, treatments, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

What is claimed:

1. An isolated polynucleotide molecule encoding a growth hormone-releasing hormone having the amino acid sequence of SEQ ID NO:1.

2. A vector comprising a promoter; a nucleotide sequence encoding SEQ ID NO:1; and a 3' untranslated region operatively linked for functional expression.

3. The vector of claim 2, wherein said vector is selected from the group consisting of a plasmid, or a viral vector.

* * * * *

SEQUENCE LISTING

```
<160> NUMBER OF SEQ ID NOS: 14
<210> SEQ ID NO 1
<211> LENGTH: 40
<212> TYPE: PRT
<213> ORGANISM: Artificial sequence
<220> FEATURE:
<223> OTHER INFORMATION: Hormone

<400> SEQUENCE: 1

His Val Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40


<210> SEQ ID NO 2
<211> LENGTH: 48
<212> TYPE: DNA
<213> ORGANISM: Artificial sequence
<220> FEATURE:
<223> OTHER INFORMATION: Primer

<400> SEQUENCE: 2

aggcagcagg gagagaggaa ccaagagcaa ggagcataat gactgcag                48


<210> SEQ ID NO 3
<211> LENGTH: 42
<212> TYPE: DNA
<213> ORGANISM: Artificial sequence
<220> FEATURE:
<223> OTHER INFORMATION: Primer

<400> SEQUENCE: 3

accctcagga tgcggcggca cgtagatgcc atcttcacca ac                      42


<210> SEQ ID NO 4
<211> LENGTH: 27
<212> TYPE: DNA
<213> ORGANISM: Artificial sequence
<220> FEATURE:
<223> OTHER INFORMATION: Primer

<400> SEQUENCE: 4
```

-continued

```
cggaaggtgc tggcccagct gtccgcc                                        27


<210> SEQ ID NO 5
<211> LENGTH: 36
<212> TYPE: DNA
<213> ORGANISM: Artificial sequence
<220> FEATURE:
<223> OTHER INFORMATION: Primer

<400> SEQUENCE: 5

ctgctccagg acatcctgaa caggcagcag ggagag                              36


<210> SEQ ID NO 6
<211> LENGTH: 358
<212> TYPE: DNA
<213> ORGANISM: Artificial sequence
<220> FEATURE:
<223> OTHER INFORMATION: Promoter

<400> SEQUENCE: 6

gagctccacc gcggtggcgg ccgtccgcct tcggcaccat cctcacgaca cccaaatatg      60

gcgacgggtg aggaatggtg gggagttatt tttagagcgg tgaggaaggt gggcaggcag     120

caggtgttgg cgctttaaaa ataactcccg ggagttattt ttagagcgga ggaatggtgg     180

acacccaaat atggcgacgg ttcctcaccc gtcgccatat ttgggtgtcc gccctcggcc     240

ggggccgcat tcctgggggc cgggcggtgc tcccgcccgc ctcgataaaa ggctccgggg     300

ccggcggcgg cccacgagct acccggagga gcgggaggcg ccaagctcta gaactagt       358


<210> SEQ ID NO 7
<211> LENGTH: 649
<212> TYPE: DNA
<213> ORGANISM: HUMAN

<400> SEQUENCE: 7

atcggggtgg catccctgtg acccctcccc agtgcctctc ctggccctgg aagttgccac      60

tccagtgccc accagccttg tcctaataaa attaagttgc atcattttgt ctgactaggt     120

gtccttctat aatattatgg ggtggagggg ggtggtatgg agcaaggggc aagttgggaa     180

gacaacctgt agggcctgcg ggtctattg ggaaccaagc tggagtgcag tggcacaatc     240

ttggctcact gcaatctccg cctcctgggt tcaagcgatt ctcctgcctc agcctcccga     300

gttgttggga ttccaggcat gcatgaccag gctcagctaa tttttgtttt tttggtagag     360

acggggtttc accatattgg ccaggctggt ctccaactcc taatctcagg tgatctaccc     420

accttggcct cccaaattgc tgggattaca ggcgtgaacc actgctccct tccctgtcct     480

tctgatttta aaataactat accagcagga ggacgtccag acacagcata ggctacctgc     540

catggcccaa ccggtgggac atttgagttg cttgcttggc actgtcctct catgcgttgg     600

gtccactcag tagatgcctg ttgaattcaa gcttatcgat accgtcgac                649


<210> SEQ ID NO 8
<211> LENGTH: 262
<212> TYPE: DNA
<213> ORGANISM: HUMAN

<400> SEQUENCE: 8

atggtgctct gggtgttctt ctttgtgatc ctcaccctca gcaacagctc ccactgctcc      60

ccacctcccc ctttgaccct caggatgcgg cggtatgcag atgccatctt caccaacagc     120
```

-continued taccggaagg tgctgggcca gctgtccgcc cgcaagctgc tccaggacat catgagcagg 180
cagcagggag agagcaacca agagcgagga gcgaggagca agggcacggc tttaatgact 240
gcaggaattc gatatcaagc tt 262

SEQ ID NO 9
<211> LENGTH: 632
<212> TYPE: DNA
<213> ORGANISM: MOUSE

<400> SEQUENCE: 9
acccttatct ttccatcatt tctttttcta acagcaaaga tcacaatgac agaagtgaat 60
gatcagaatg taaaaatatt tgtgcaaaat tgcattaact gttctcacca tctaatcggg 120
gtacaacctc aaacacaacg gccataatga agaaaagcta cactggaagt tctagatgtc 180
atctggctcc cacaacatca cagagtccca cccaggagtg aaggatgctg ctctgggtgc 240
tctttgtgat cctcatcctc accagtggct cccactgctc actgcccccc tcacctccct 300
tcaggatgca gcgacacgta gatgccatct tcaccaccaa ctacaggaaa ctcctgagcc 360
agctgtatgc ccggaaagtg atccaggaca tcatgaacaa gcaaggggag aggatccagg 420
aacaaagggc caggctcagc cgccaggaag acagcatgtg gacagaggac aagcagatga 480
ccctggagag catcttgcag ggattcccaa ggatgaagcc ttcagcggac gcttgagccc 540
cccgagcccc aaacacaact gtaccctgtt acttctgctt cagctctgac cttttccgtc 600
ctctgtaaat acaataaaac ccccattctc at 632

<210> SEQ ID NO 10
<211> LENGTH: 391
<212> TYPE: DNA
<213> ORGANISM: BOS TAURUS

<400> SEQUENCE: 10
ctcaccctca gcagcggctc ccacggttcc ctgccttccc agcctctcag gtaagcagtt 60
ctgagaagag aagcaagaga ggccctttga ggatgcagac tcgagctggt ccccagctgg 120
gtcctcaggc agcctccctt gctcatctct gggagggtgg cagactgagc cccagagagg 180
tcaccaccca gccctggttc cagccctctc tggggacgag cagggcaaga ggcgacagaa 240
agacctcaca gagaccaagt gagcacagtc ccctgggcct cccaccccac cctttgacct 300
ctgactcctt ctactaggat tccacggtac gcagatgcca tcttcactaa cagctaccgg 360
aaggttctgg gccagctgtc tgcccgcaac t 391

<210> SEQ ID NO 11
<211> LENGTH: 392
<212> TYPE: DNA
<213> ORGANISM: BOS TAURUS

<400> SEQUENCE: 11
ctcaccctca gcagcggctc ccacgggttc cctgccttcc caagcctctc aggtaagcag 60
ttctgagaag agaagcaaga gaggcccttt gaggatgcga ctcgagctgg tccccagctg 120
ggtcctcagg cagcctccct tgctcatctc tgggagggtg gcagactgag ccccagagag 180
gtcaccaccc agccctggtt ccagccctct ctggggacga gcagggcaag aggcgacaga 240
aagacctcac agagaccaag tgagcacagt cccctgggcc tcccacccca ccctttgacc 300

-continued

```
tctgactcct tctactagga ttccacggta cgcagatgcc atcttcacta acagctaccg    360

gaaggttctg ggccagctgt ctgcccgcaa ct                                  392


<210> SEQ ID NO 12
<211> LENGTH: 88
<212> TYPE: DNA
<213> ORGANISM: EQUUS CABALLUS

<400> SEQUENCE: 12

atgcagatgc catcttcacc aacaactacc ggaaggtgct gggccagctc tctgcccgca     60

agatcctcca ggacatcatg agcaggca                                        88


<210> SEQ ID NO 13
<211> LENGTH: 511
<212> TYPE: DNA
<213> ORGANISM: RATTUS NORVEGICUS

<400> SEQUENCE: 13

ctgcggatgc cacggaacat cgagccaaat cccaggaaca cgctctgaac cccaggagct     60

gcacaccact ctattaggtc ccgcccagga gtgaaggatg ccactctggg tgttctttgt    120

gctcctcacc ctcaccagtg gctcccactg ctcactgccc ccctcacctc ccttcagggt    180

gcggcggcat gcagacgcca tcttcaccag cagctaccgg agaatcctgg gccaattata    240

tgcccgcaaa ctgctgcacg aaatcatgaa caggcagcaa ggggagagga accaggaaca    300

aagatccagg ttcaaccgcc atttggacag agtgtgggca gaggacaagc agatggccct    360

ggagagcatc ttgcagggat tcccaaggat gaagctttca gcggaggctt gagccctcgg    420

cccccaaaca tagctggacc ctgttacttc tacttcagtt ctgatcttct ccttcctctg    480

tgaatacaat aaagacccag ttctcatctg c                                   511


<210> SEQ ID NO 14
<211> LENGTH: 40
<212> TYPE: PRT
<213> ORGANISM: PIG

<400> SEQUENCE: 14

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Arg Asn Gln Glu Gln Gly Ala
        35                  40
```